US009474270B2

(12) United States Patent
Spooner-Hart et al.

(10) Patent No.: US 9,474,270 B2
(45) Date of Patent: Oct. 25, 2016

(54) METHODS AND COMPOSITIONS FOR CONTROLLING PESTS

(71) Applicant: Bio-Gene Technology Ltd, Hillarys, Western Australia (AU)

(72) Inventors: Robert Neil Spooner-Hart, Kurrajong (AU); Albert Habib Basta, Glenwood (AU)

(73) Assignees: Bioprosepect Limited, Perth, Western Australia (AU); University of Western Sydney, South Penrith DC, New South Wales (AU)

( * ) Notice: Subject to any disclaimer, the term of this patent is extended or adjusted under 35 U.S.C. 154(b) by 50 days.

(21) Appl. No.: 14/250,187

(22) Filed: Apr. 10, 2014

(65) Prior Publication Data

US 2014/0336269 A1    Nov. 13, 2014

Related U.S. Application Data

(63) Continuation of application No. 13/431,726, filed on Mar. 27, 2012, now abandoned, which is a continuation of application No. 12/782,125, filed on May 18, 2010, now abandoned, which is a continuation of application No. 12/134,035, filed on Jun. 5, 2008, now Pat. No. 7,820,209, which is a continuation of application No. 10/477,057, filed as application No. PCT/AU02/00569 on May 8, 2002, now abandoned.

(30) Foreign Application Priority Data

May 8, 2001    (AU) ........................................ PR4842

(51) Int. Cl.
| | | |
|---|---|---|
| A01N 65/00 | (2009.01) | |
| A61K 36/61 | (2006.01) | |
| A01N 35/06 | (2006.01) | |
| A01N 35/10 | (2006.01) | |
| A01N 37/18 | (2006.01) | |
| A01N 65/04 | (2009.01) | |
| A01N 65/08 | (2009.01) | |
| A01N 65/10 | (2009.01) | |
| A01N 65/12 | (2009.01) | |
| A01N 65/22 | (2009.01) | |
| A01N 65/28 | (2009.01) | |
| A01N 65/36 | (2009.01) | |
| A01N 65/42 | (2009.01) | |
| A01N 65/48 | (2009.01) | |

(52) U.S. Cl.
CPC .............. *A01N 35/06* (2013.01); *A01N 35/10* (2013.01); *A01N 37/18* (2013.01); *A01N 65/04* (2013.01); *A01N 65/08* (2013.01); *A01N 65/10* (2013.01); *A01N 65/12* (2013.01); *A01N 65/22* (2013.01); *A01N 65/28* (2013.01); *A01N 65/36* (2013.01); *A01N 65/42* (2013.01); *A01N 65/48* (2013.01); *A61K 36/61* (2013.01)

(58) Field of Classification Search
CPC .............................. A61K 36/61; A01N 65/28
USPC ........................................................ 424/742
See application file for complete search history.

(56) References Cited

U.S. PATENT DOCUMENTS

| | | | |
|---|---|---|---|
| 4,202,840 | A | 5/1980 | Gray et al. |
| 4,780,127 | A | 10/1988 | Michaely et al. |
| 4,797,150 | A | 1/1989 | Carter |
| 4,853,028 | A | 8/1989 | Carter |
| 5,411,728 | A | 5/1995 | Joulain et al. |
| 5,416,061 | A | 5/1995 | Hewett |
| 5,426,091 | A | 6/1995 | Barton |
| 6,054,137 | A | 4/2000 | Breton et al. |
| 6,180,568 | B1 | 1/2001 | Takahashi et al. |
| 6,218,579 | B1 | 4/2001 | Jones |
| 6,291,400 | B1 | 9/2001 | Barton et al. |
| 6,352,727 | B1 | 3/2002 | Takahashi |
| 6,444,216 | B2 | 9/2002 | Reifenrath |

FOREIGN PATENT DOCUMENTS

| | | |
|---|---|---|
| EP | 0 613 680 B1 | 10/1997 |
| WO | 93/24446 A1 | 12/1993 |
| WO | 99/18802 A1 | 4/1999 |
| WO | 00/27206 A1 | 5/2000 |

OTHER PUBLICATIONS

Douglas et al. (Defining North Island manuka chemotype resources, Crop and Food Research Report No. 447, Jul. 2001).*

(Continued)

Primary Examiner — Johann R Richter
Assistant Examiner — Danielle Sullivan
(74) Attorney, Agent, or Firm — Knobbe Martens Olson & Bear LLP

(57) ABSTRACT

The present invention is directed to pest-controlling compositions comprising as active ingredients one or more β-diones, particularly β-diketones and β-triketones, and to the use of these compositions inter alia for preventing, eradicating, destroying, repelling or mitigating harmful, annoying or undesired pests including insects, arachnids, helminths, molluscs, protozoa and viruses. The present invention is further directed to processes of preparing β-diones by de novo synthesis or from natural sources such as volatile oil-bearing plants from families including Alliaceae, Apiaceae, Asteraceae, Cannabinaceae, Lamiaceae, Pteridaceae, Myrtaceae, Myoporaceae, Proteaceae, Rutaceae and Zingiberaceae.

2 Claims, 4 Drawing Sheets

(56) References Cited

OTHER PUBLICATIONS

Ahmed, S.M., et al., "Vapor toxicity and repellency of some essential oils to insect pests", STN CAPLUS, vol. 15, No. 105, 1988, No. 105 XP002089702 (Abstract).
Bloor, S.J., "Antiviral Phloroglucinois from New Zealand Kunzee species", J Nat Prod, vol. 55, 1992, pp. 43-47.
Bignell, C.M. et al. 1997 Flav Frag Journal 12:177-183.
Boland, D. et al. 1993 American Chemical Society 525:72-87.
Brophy, J.J. et al. 1990 J Essent Oil Res 2:87-90.
Brophy, J.J. et al. 1995 J Essent Oil Res 7:237-254.
Duke, S.O., et al., "Natural products as sources of herbicides: current status and status and future trends", Weed Research, vol. 40, 2000, pp. 99-111.
Ghisalberti, E.L., "Bioactive Acylphloroglucinol derivatives from Eucalyptus species", Phytochemistry, vol. 41, pp. 7-22.
Hellyer, R. 1968 Aust J Chem 21(11) 2825-2828.
Keramaris, K.E., et al., "Egg laying suppression in *Drosophila melanogaster* (Diptera:Drosophilidae) and Dacus (Bactrocera) oleae (Diptera: Tephritidae) by phloroglucinol, a peroxidase inhibitor", Bull Entomological Res, vol. 86, 1996, pp. 369-375.
Porter, N.G., et al., "Chemical, physical and antimicrobial properties of essential oils of Leptosppernum scoparium and Kunzea ericoldes", Phytochemistry, vol. 50, 1998, pp. 407-415.

Southwell, I.A. et al. 2000 J Essent Oil Res 12:267-278.
Doran, Cajuput Oil, Harwood Academic Publishers, 1999, pp. 221-233.
Villar et al. Toxicity of melaleuca oil and related essential oils applied topically on dogs and cats, Veterinary and human toxicology, vol. 36, Apr. 1994, pp. 139-142.
Douglas et al. Defining North Island Manuka Chemotype Resources, Crop and Food Research Report, No. 447, Jul. 2001.
Noel G. Porter and Alistair L. Wilkins, "Chemical, physical and antimicrobial properties of essential oils of Leptospermum scoparium and Kunzea ericoides," Phytochemistry 50 (1998) 407-415.
Perry et al., "Essential Oils from New Zealand Manuka and Kanuka: Chemotaxonomy of Leptospermum," Phytochemistry 44:8 (1997) 1485-1494.
Douglas et al., "Essential oils from New Zealand manuka: triketone and other chemotypes of Leptospermum scoparium," Phytochemistry 65 (2004) 1255-1264.
Briggs et al., "Leptospermone. Part II", Leptospermum Phenolic Oils, J. Chem Soc., 1945.
Khambay et al., "A New Insecticidal Pyranocyclohexenedione from Kunzea ericifolia," J. Nat. Prod. 62 (1999) 1423-1424.

\* cited by examiner $^1$H NMR Data (CDCl$_3$, 500MHz)

|  | Major Isomer | | Minor Isomer | |
|---|---|---|---|---|
| $^1$H (see below) | Signal (ppm) | Integral | Signal (ppm) | Integral |
| A | 19.18 | 0.89 | 18.45 | 0.48 |
| B | 3.98 | 1.09 | 3.85 | 0.55 |
| C | 3.96 | 2.75 | 3.87 | 1.55 |
| D | 1.97 | 3.00 | 1.92 | 1.72 |
| E | 1.34 | 6.43 | 1.46 | 3.52 |
| F | 1.15 | 6.13 | 1.17 | 3.48 |

MAJOR

MINOR

METHODS AND COMPOSITIONS FOR CONTROLLING PESTS

CROSS-REFERENCE TO RELATED APPLICATIONS

This application is a continuation of U.S. application Ser. No. 13/431,726, filed Mar. 27, 2012, which is a continuation of U.S. application Ser. No. 12/782,125, filed May 18, 2010, which is a continuation of U.S. application Ser. No. 12/134, 035, filed Jun. 5, 2008, and granted Oct. 26, 2010 as U.S. Pat. No. 7,820,209, which is a continuation of U.S. application Ser. No. 10/477,057, filed Sep. 23, 2004. U.S. application Ser. No. 10/477,057 is the U.S. National Phase under 35 U.S.C. §371 of International Application No. PCT/AU02/00569, filed May 8, 2002 designating the U.S. and published in English as WO 02/089587, which claims priority to Australian Patent Application PR 4842, filed May 8, 2001. This application incorporates herein by reference U.S. application Ser. Nos. 13/431,726, 12/782,125, 12/134,035, and 10/477,057, U.S. Pat. No. 7,820,209, International Application No. PCT/AU02/00569 including the International Publication No. WO 02/089587, and Australian Patent Application PR 4842 in their entireties.

FIELD OF THE INVENTION

This invention relates generally to methods and compositions for controlling pests. More particularly, the present invention relates to pest-controlling compositions comprising as active ingredients one or more β-diones, particularly β-diketones and β-triketones, and to the use of these compositions inter alia for preventing, eradicating, destroying, repelling or mitigating harmful, annoying or undesired pests including insects, arachnids, helminths, molluscs, protozoa and viruses. The present invention further relates to processes of preparing β-diones by de novo synthesis or from natural sources such as volatile oil-bearing plants from families including Alliaceae, Apiaceae, Asteraceae, Cannabinaceae, Lamiaceae, Pteridaceae, Myrtaceae, Myoporaceae, Proteaceae, Rutaceae and Zingiberaceae. Bibliographic details of various publications referred to in this specification are collected at the end of the description.

BACKGROUND OF THE INVENTION

Triketones have been used for many years as herbicides for the control of undesired vegetation. Herbicidal triketones have been described, for example, in EP-A-338992, EP-A-336898, U.S. Pat. No. 4,869,748, EP-A-186118, EP-A-186119, EP-A-186120, U.S. Pat. No. 4,202,840, U.S. Pat. No. 4,695,673, U.S. Pat. No. 4,780,127, U.S. Pat. No. 4,921,526, U.S. Pat. No. 5,006,150, U.S. Pat. No. 5,545,607, U.S. Pat. No. 5,925,795, U.S. Pat. No. 5,990,046, U.S. Pat. No. 6,218,579, EP-A-249150, EP-A-137963, EP-A-394889, EP-A-506907 or EP-B-135191. Examples of herbicidal triketones are inter alia Sulcotrione (MIKADO®) whose chemical designation is 2-(2-chloro-4-methanesulfonylbenzoyl)-1,3-cyclohexandione, 2-(4-methylsulfonyloxy-2-nitrobenzoyl)-4,4,6,6-tetramethyl-1,3-cyclohexane dione; 3-(4-methylsulfonyloxy-2-nitrobenzoyl)-bicyclo-[3,2,1]octane-2,4-dione; 3-(4-methylsulfonyl-2-nitrobenzoyl)-bicyclo-[3,2,1]octane-2,4-dione; 4-(4-chloro-2-nitrobenzoyl)-2,6,6-trimethyl-2H-1,2-oxazine-3,5(4H, 6H)-dione; 3-(4-methylthio-2-nitrobenzoyl)-bicyclo[3,2,1]octane-2,4-dione; 4-(2-nitro-4-trifluoromethoxybenzoyl)-2,6,6-trimethyl-2H-1,2-oxazine-3,5(4H, 6H)-dione.

SUMMARY OF THE INVENTION

The instant invention is predicated in part on the discovery that β-diones, particularly β-diketones and β-triketones, such as those obtainable from volatile oil-bearing plants including plants from the families Alliaceae, Apiaceae, Asteraceae, Cannabinaceae, Lamiaceae, Pteridaceae, Myrtaceae, Myoporaceae, Proteaceae, Rutaceae and Zingiberaceae, exhibit significant pesticidal, especially insecticidal, arachnicidal, helminthicidal and/or molluscicidal activity. This discovery has been reduced to practice in novel pest-controlling compositions and methods for their preparation and use, as described hereinafter.

DETAILED DESCRIPTION OF THE INVENTION

Figure 1:
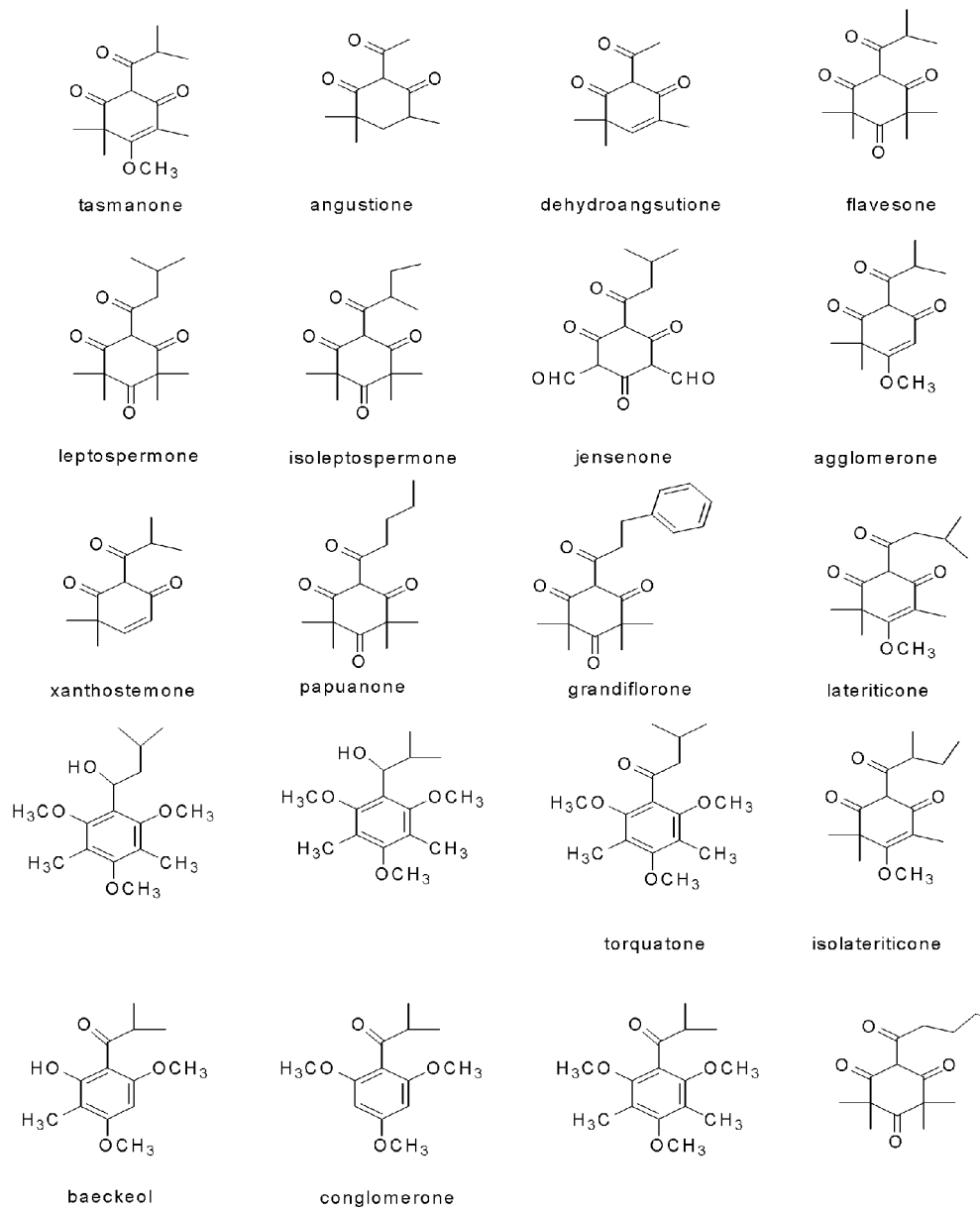
FIG. 1 shows the structures relating to the major constituents of the published Myrtaceae essential oils.

One aspect of the present invention contemplates the use of a β-dione compound, particularly a β-diketone or a β-triketone compound, in the preparation of a composition for controlling harmful, annoying or undesired pests, said compound being represented by the general formula (I)

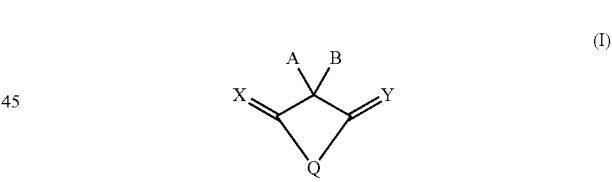

wherein

A is (C=O)R$_1$, (C=S)R$_1$, OR$_2$, SR$_2$, (CR$_3$NR$_4$R$_5$), C(R$_3$)$_2$OR$_2$, NR$_4$R$_5$, (C=N—R$_4$)R$_1$, N=O, N(=O)$_2$, NR$_4$OR$_2$ or SO$_4$R$_2$;

R$_1$ is selected from H, C$_1$-C$_{10}$ alkyl, C$_2$-C$_{10}$ arylalkyl, C$_3$-C$_6$ cycloalkyl, C$_2$-C$_{10}$ alkenyl, C$_2$-C$_{10}$ heteroarylalkyl, C$_1$-C$_{10}$ haloalkyl, C$_1$-C$_{10}$ dihaloalkyl, C$_2$-C$_{10}$ trihaloalkyl, C$_2$-C$_{10}$ haloalkoxy, C$_1$-C$_{10}$ hydroxyalkyl, C$_1$-C$_{10}$ thioalkyl and C$_1$-C$_{10}$ nitroalkyl, OR$_2$, SR$_2$, (CR$_3$NR$_4$R$_5$), NR$_4$R$_5$, (C=N—R$_4$)R$_6$, N=O, N(=O)$_2$, NR$_4$OR$_7$ or SO$_4$R$_7$;

R$_2$ is selected from H, C$_1$-C$_{10}$ alkyl, C$_2$-C$_{10}$ arylalkyl, C$_3$-C$_6$ cycloalkyl, C$_2$-C$_{10}$ alkenyl, C$_2$-C$_{10}$ heteroarylalkyl, C$_2$-C$_{10}$ haloalkyl, C$_2$-C$_{10}$ dihaloalkyl, C$_2$-C$_{10}$ trihaloalkyl, (CR$_3$NR$_4$R$_5$), NR$_4$R$_5$, (C=N—R$_4$)R$_6$, N=O, N(=O)$_2$ or NR$_4$OR$_7$;

R$_3$ is selected from H, C$_1$-C$_{10}$ alkyl, C$_2$-C$_{10}$ arylalkyl, C$_3$-C$_6$ cycloalkyl, C$_2$-C$_{10}$ alkenyl, C$_2$-C$_{10}$ heteroarylalkyl, C$_2$-C$_{10}$ haloalkyl, C$_2$-C$_{10}$ dihaloalkyl, C$_2$-C$_{10}$ trihaloalkyl, $C_2$-$C_{10}$ haloalkoxy, $OR_7$, $SR_7$, $(CR_8NR_4R_5)$, $NR_4R_5$, $(C=N-R_4)R_6$, $N=O$, $N(=O)_2$, $NR_4OR_7$ or $SO_4R_7$;

$R_4$ and $R_5$ are independently selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $OR_7$ or $SR_7$;

$R_6$ is selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $C_2$-$C_{10}$ haloalkoxy, $OR_7$, $SR_7$, $(CR_8NR_9R_{10})$, $NR_9R_{10}$ or $NR_9OR_7$;

$R_7$ is selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl;

$R_8$ is selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $OR_{11}$, $SR_{11}$ or $NR_9R_{10}$;

$R_9$ and $R_{10}$ are independently selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $OR_{12}$ or $SR_{12}$;

$R_{11}$ is selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl;

$R_{12}$ is selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl;

B is H, $C_1$-$C_{10}$ alkyl, $C_2$-$C_{10}$ alkenyl, aryl or heteroaryl;

X and Y are independently selected from oxygen, sulfur, $-N-R_4$; and

Q completes a 5-8-member saturated or unsaturated carbocyclic or heterocyclic ring in which optionally one or more members comprise $-C(=X)-$; and wherein Q is optionally substituted with one or more substituents selected from $C_1$-$C_{10}$ alkyl, $C_3$-$C_6$ cycloalkyl, $C_2$-$C_{10}$ alkenyl, $C_2$-$C_{10}$ haloalkyl, $C_2$-$C_{10}$ dihaloalkyl, $C_2$-$C_{10}$ trihaloalkyl, $C_2$-$C_{10}$ haloalkoxy, $OR_2$, $SR_2$, $(CR_3NR_4R_5)$, $NR_4R_5$, $(C=N-R_4)R_1$, $N=O$, $N(=O)_2$, $NR_4OR_2$, $SO_4R_2$, $C_2$-$C_{10}$ 1-arylalkyl, $C_2$-$C_{10}$ 2-arylalkyl or $(C=X)R_1$.

Heterocyclic systems can be optionally attached to a moiety other than those set forth above via a carbon atom or a heteroatom of $R_1$ to $R_{11}$.

Preferred compounds represented by formula (I) are β-diketones and especially preferred are β-triketones.

As used herein, the term "alkyl" refers to linear or branched chains. The term "haloalkyl" refers to an alkyl group substituted by at least one halogen. Similarly the term "haloalkoxy" refers to an alkoxy group substituted by at least one halogen. As used herein the term "halogen" refers to fluorine, chlorine, bromine and iodine.

As used herein the term "aryl" refers to aromatic carbocyclic ring systems such as phenyl or naphthyl, anthracenyl, especially phenyl. Suitably, aryl is $C_6$-$C_{14}$ with mono, di, tri, tetra and penta substitution containing $OR_2$, F, Cl, Br, I, $NO_2$, $CF_3$, $COR_1$, $NR_4R_5$, $SO_2R_2$, $SR_2$.

As used herein the terms "heterocycle", "heterocyclic", "heterocyclic systems" and the like refer to a saturated, unsaturated, or aromatic carbocyclic group having a single ring, multiple fused rings (for example, bicyclic, tricyclic, or other similar bridged ring systems or substituents), or multiple condensed rings, and having at least one heteroatom such as nitrogen, oxygen, or sulfur within at least one of the rings. This term also includes "heteroaryl" which refers to a heterocycle in which at least one ring is aromatic. Any heterocyclic or heteroaryl group can be unsubstituted or optionally substituted with one or more groups, as defined above. Further, bi- or tricyclic heteroaryl moieties may comprise at least one ring, which is either completely, or partially, saturated. Suitable heteroaryl moieties include, but are not limited to oxazolyl, thiazaoyl, thienyl, furyl, 1-isobenzofuranyl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indoyl, indolyl, purinyl, phthalazinyl.

The articles "a" and "an" are used herein to refer to one or to more than one (i.e., to at least one) of the grammatical object of the article. By way of example, "an element" means one element or more than one element.

A preferred carbocyclic ring formed by Q is an optionally substituted cyclohexanedione.

A preferred subgroup of compounds of formula (I) is represented by formula (II)

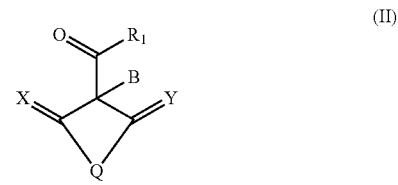

Such compounds may exist in a number of tautomeric forms. For example, in the case wherein X and Y are each oxygen, and B is hydrogen, then the compounds of formula II may exist as one or more of the structural formulae shown below.

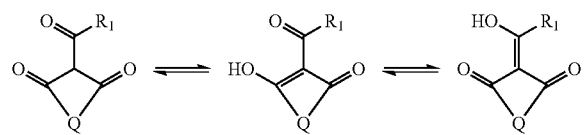

It is intended that all such tautomeric structures are included within the scope of the present invention.

It should also be appreciated that some of the compounds of formula (I) are capable of existing as different geometric isomers and diastereomers. The invention thus includes both the individual isomers and mixtures of such isomers.

Another preferred subgroup of compounds of formula (I) is represented by formula (III)

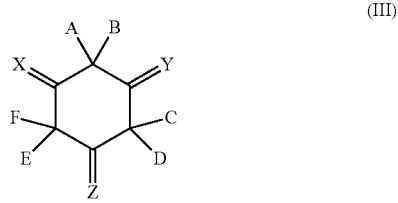

wherein

X, Y and Z are each independently selected from oxygen, sulfur, $-N-R_4$ or one of $C=X$, $C=Y$ or $C=Z$ is $CH_2$;

A is $(C=O)R_1$, $(C=S)R_1$, $OR_2$, $SR_2$, $(CR_3NR_4R_5)$, $C(R_3)_2OR_2$, $NR_4R_5$, $(C=N-R_4)R_1$, $N=O$, $N(=O)_2$, $NR_4OR_2$ or $SO_4R_2$;

B is as defined above;

C, D, E and F are each independently selected from H, $C_1$-$C_{10}$ alkyl, $C_3$-$C_6$ cycloalkyl, $C_2$-$C_{10}$ alkenyl, $C_2$-$C_{10}$ haloalkyl, $C_2$-$C_{10}$ dihaloalkyl, $C_2$-$C_{10}$ trihaloalkyl, $OR_2$, $SR_2$, $(CR_3NR_4R_5)$, $NR_4R_5$, $(C=N-R_4)R_1$, $N=O$, $N(=O)_2$, $NR_4OR_2$, $SO_4R_2$, $C_2$-$C_{10}$ 1-arylalkyl, $C_2$-$C_{10}$ 2-arylalkyl or $(C=X)R_1$; and $R_1$, $R_2$, $R_2$, $R_4$ and $R_5$ are as defined above.

Preferred β-diones represented by formula (III) are flavesone (1-isobutyroyl-3,3,5,5-tetramethylcyclohexan-2,4,6-trione), isoleptospermone (1-isovaleroyl-3,3,5,5-tetramethylcyclohexan-2,4,6-trione), leptospermone (1-valeroyl-3,3,5,5-tetramethylcyclohexan-2,4,6-trione), papuanone (1-pentoyl-3,3,5,5-tetramethylcyclohexan-2,4,6-trione), grandiflorone (1-(2-phenylethyl)-3,3,5,5-tetramethylcyclohexan-2,4,6-trione) and jensenone (1-valeroyl-3,5-dicarbonylcyclohexan-2,4,6-trione), including analogues and derivatives thereof.

By way of example, flavesone analogues contemplated by the present invention include, but are not restricted to, compounds having the following structural formulae, wherein the structural formula of flavesone is shown for comparative purposes:

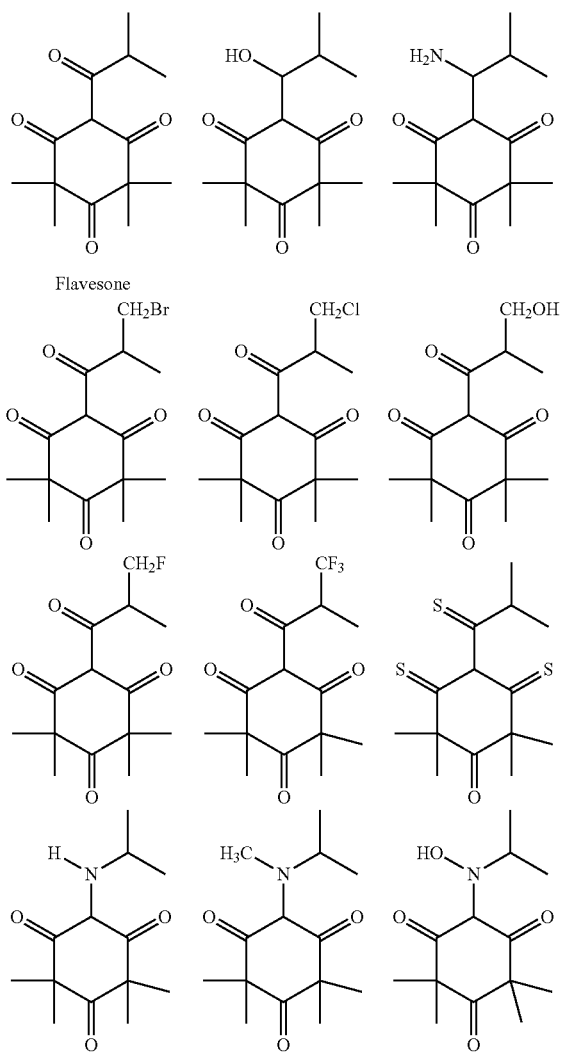

Flavesone

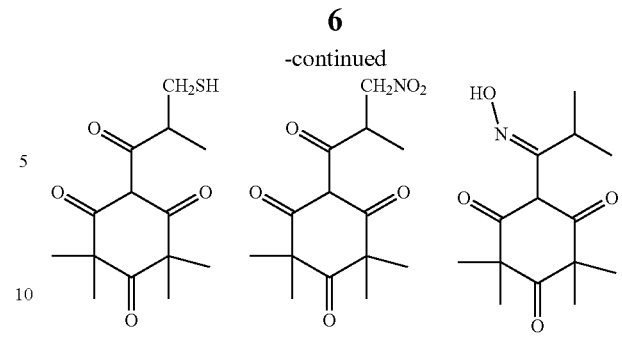

Non-limiting examples of isoleptospermone analogues contemplated by the present invention include, but are not restricted to, compounds having the following structural formulae, wherein the structural formula of isoleptospermone is shown for comparative purposes:

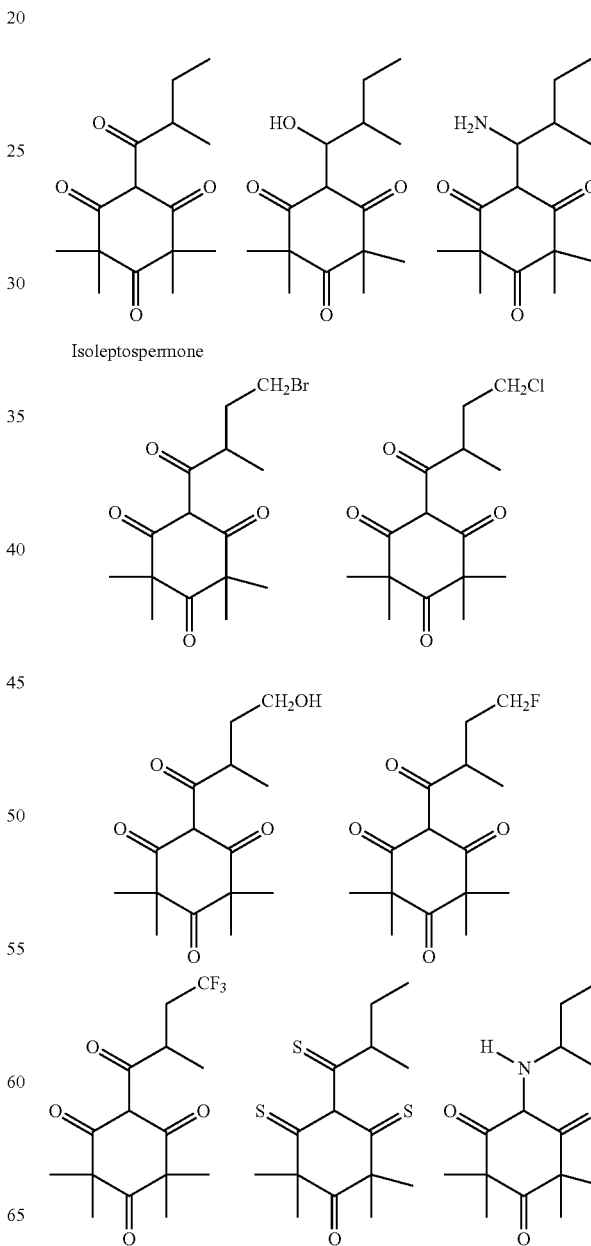

Isoleptospermone

-continued

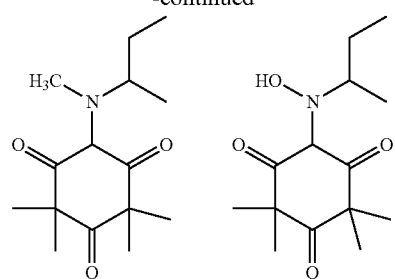

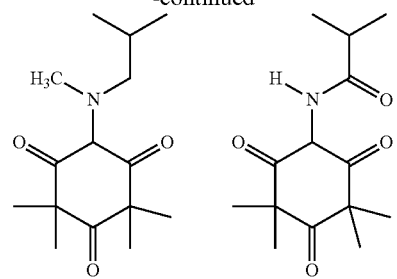

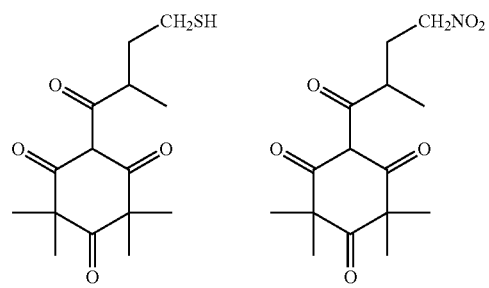

Non-limiting examples of leptospermone analogues contemplated by the present invention include, but are not restricted to, compounds having the following structural formulae, wherein the structural formula of leptospermone is shown for comparative purposes:

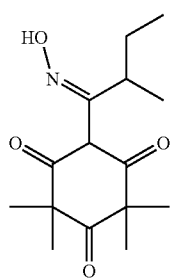

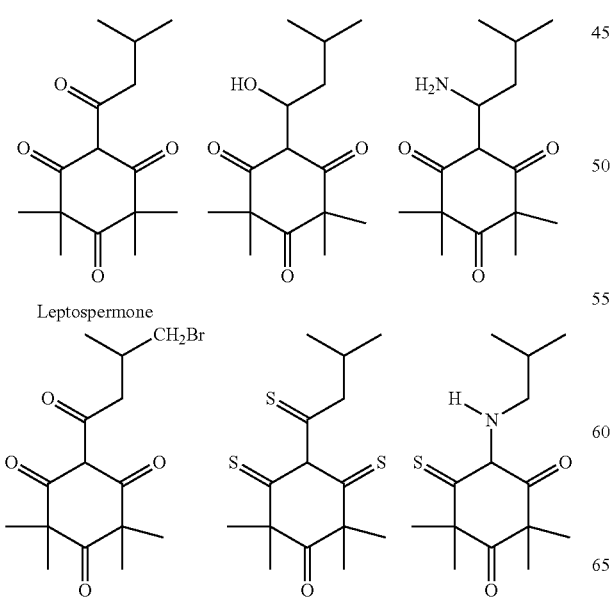

Leptospermone

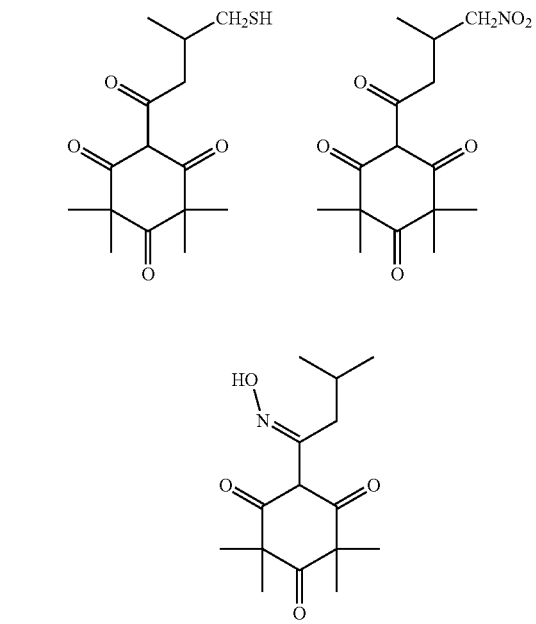

Non-limiting examples of jensenone analogues contemplated by the present invention include, but are not restricted to, compounds having the following structural formulae, wherein the structural formula of jensenone is shown for comparative purposes:

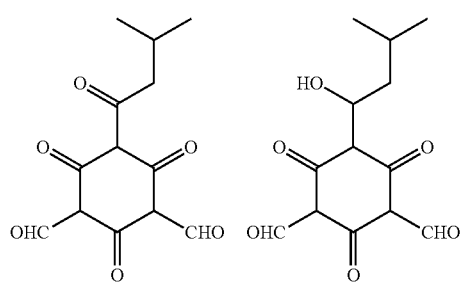
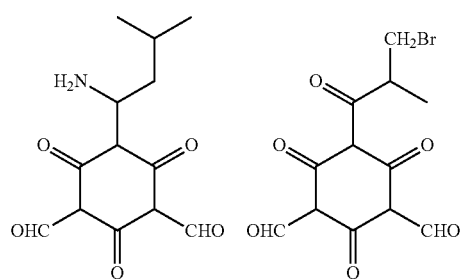
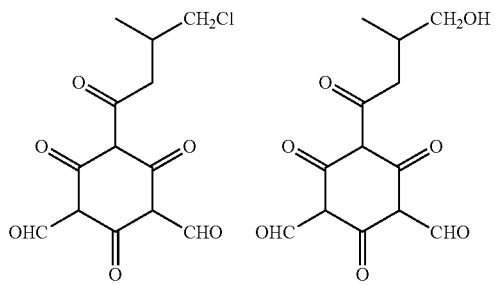
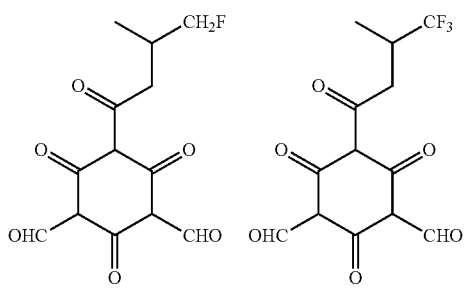
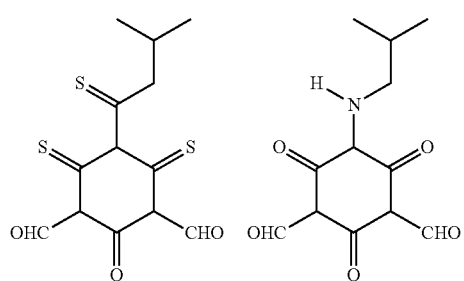

Jensenone

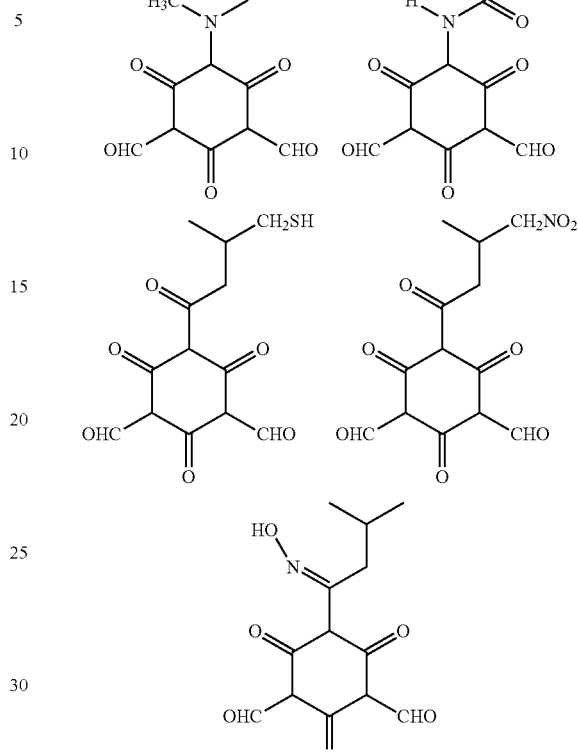

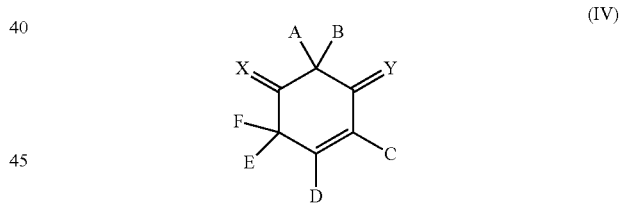

Another preferred subgroup of compounds of formula (I) is represented by formula (IV)

$$\text{(IV)}$$

wherein

X and Y are each independently selected from oxygen, sulfur —N—$R_4$ or one of C═X or C═Y is $CH_2$;

A is (C═O)$R_1$, (C═S)$R_1$, O$R_2$, S$R_2$, (C$R_3$N$R_4$$R_5$), C($R_3$)$_2$O$R_2$, N$R_4$$R_5$, (C═N—$R_4$)$R_1$, N═O, N(═O)$_2$, N$R_4$O$R_2$ or SO$_4$$R_2$;

B is as defined above;

C, D, E and F are each independently selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $C_2$-$C_{10}$ haloalkoxy, O$R_2$, S$R_2$, (C$R_3$N$R_4$$R_5$), N$R_4$$R_5$, (C═N—$R_4$)$R_1$, N═O, N(═O)$_2$, N$R_4$O$R_2$, SO$_4$$R_2$; and $R_1$, $R_2$, $R_2$, $R_4$ and $R_5$ are as defined above.

Preferred β-diones represented by formula (IV) are tasmanone (1-isobutroyl-4-methoxy-3,5,5-trimethylcyclohex-3-en-2,6-dione), agglomerone (1-isobutroyl-4-methoxy-5,5-dimethylcyclohex-3-en-2,6-dione), lateriticone (1-valeroyl-4-methoxy-3,5,5-trimethylcyclohex-3-en-2,6-dione), isolateriticone (1-isovaleroyl-4-methoxy-3,5,5-trimethylcyclohex-3-en-2,6-dione and platyphyllol (6,6-dimethyl-2-acetyl-5-methoxycyclohex-4-ene-1,3-dione), including analogues and derivatives thereof.

Non-limiting examples of tasmanone analogues contemplated by the present invention include, but are not restricted to, compounds having the following structural formulae, wherein the structural formula of tasmanone is shown for comparative purposes:

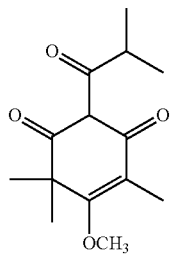
Tasmanone
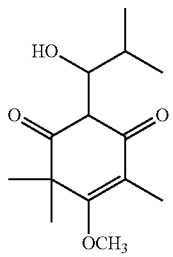

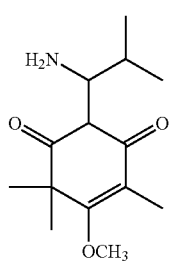
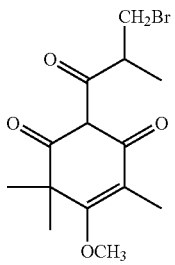

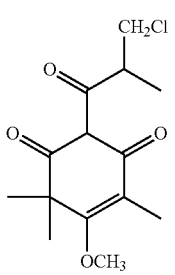
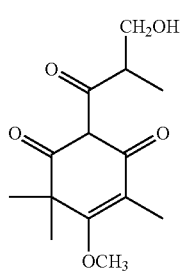

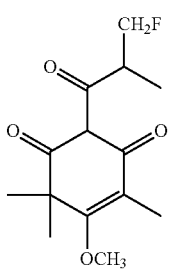
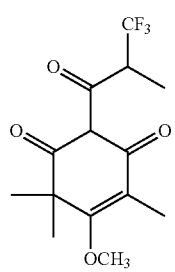

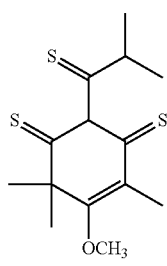
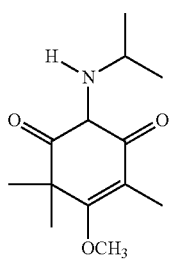

-continued

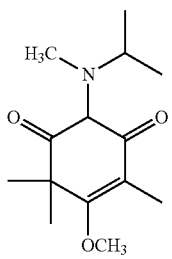
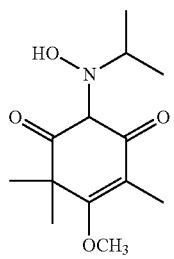

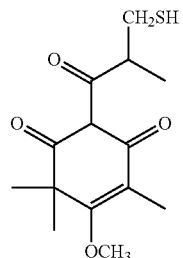
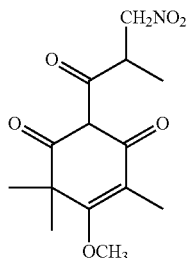

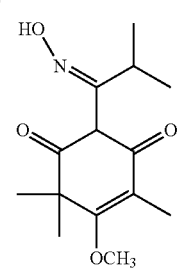

Another preferred subgroup of compounds of formula (I) is represented by formula (V)

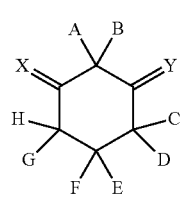

(V)

wherein

X and Y are independently selected from oxygen, sulfur or —N—$R_4$; and

A is (C=O)$R_1$, (C=S)$R_1$, O$R_2$, S$R_2$, (C$R_3$N$R_4$$R_5$), C($R_3$)$_2$O$R_2$, N$R_4$$R_5$, (C=N—$R_4$)$R_1$, N=O, N(=O)$_2$, N$R_4$O$R_2$ or SO$_4$$R_2$;

B is as defined above;

C, D, E, F, G and H are each independently selected from H, $C_1$-$C_{10}$ alkyl, $C_2$-$C_{10}$ arylalkyl, $C_3$-$C_6$ cycloalkyl, $C_2$-$C_{10}$ alkenyl, $C_2$-$C_{10}$ heteroarylalkyl, $C_2$-$C_{10}$ haloalkyl, $C_2$-$C_{10}$ dihaloalkyl, $C_2$-$C_{10}$ trihaloalkyl, $C_2$-$C_{10}$ haloalkoxy, O$R_2$, S$R_2$, (C$R_3$N$R_4$$R_5$), N$R_4$$R_5$, (C=N—$R_4$)$R_1$, N=O, N(=O)$_2$, N$R_4$O$R_2$ or SO$_4$$R_2$; and $R_1$, $R_2$, $R_2$, $R_4$ and $R_5$ are as defined above.

More specifically unsaturation, epoxides and thioepoxides may exist at positions designated by H (or G) connected to F (or E) or F (or E) connected to C (or D). A four-membered ring forming a part of a bicyclic structure may exist at positions designated by H (or G) connected to C (or D).

Preferred β-diones represented by formula (V) are angustione (1-acetyl-3,5,5-trimethylcyclohex-2,6-dione), dehydroangustione (1-acetyl-3,5,5-trimethylcyclohex-3-en-2,6-dione) and xanthostemone (1-isobutroyl-5,5-dimethylcyclohex-3-en-2,6-dione), including their analogues and derivatives.

By way of example, angustione analogues contemplated by the present invention include, but are not restricted to, compounds having the following structural formulae, wherein the structural formula of angustione is shown for comparative purposes:

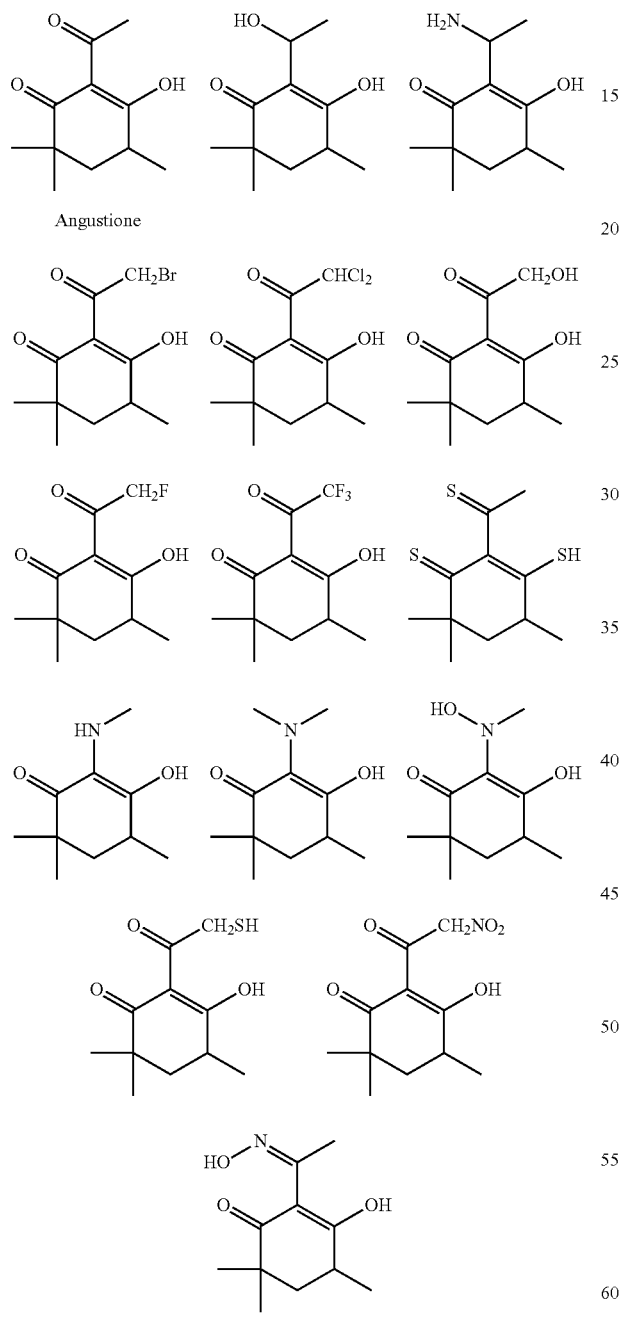

Non-limiting examples of dehydroangustione analogues include, but are not restricted to, compounds having the following structural formulae, wherein the structural formula of dehydroangustione is shown for comparative purposes:

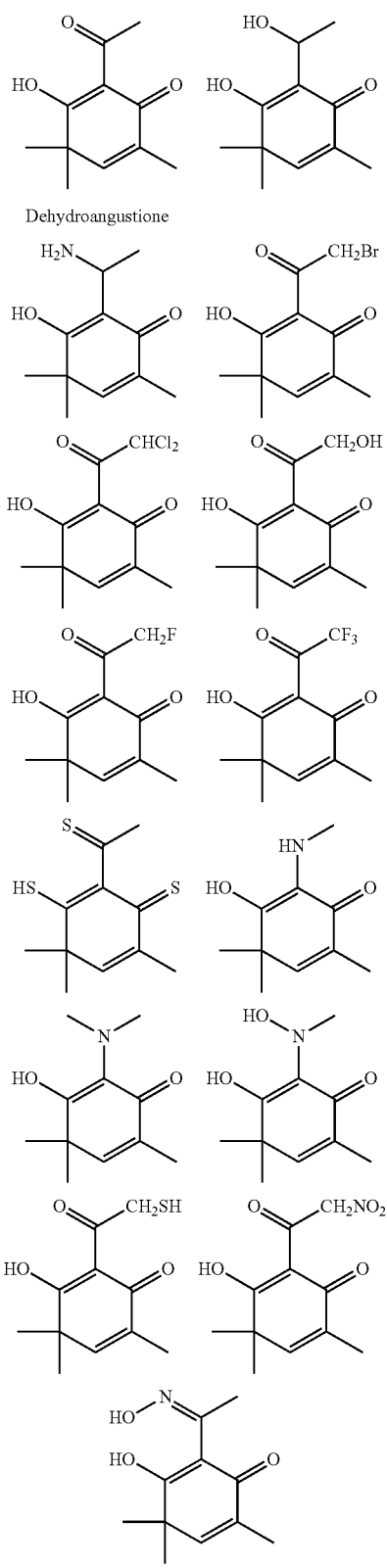

Non-limiting examples of xanthostemone analogues include, but are not restricted to, compounds having the following structural formulae, wherein the structural formula of xanthostemone is shown for comparative purposes:

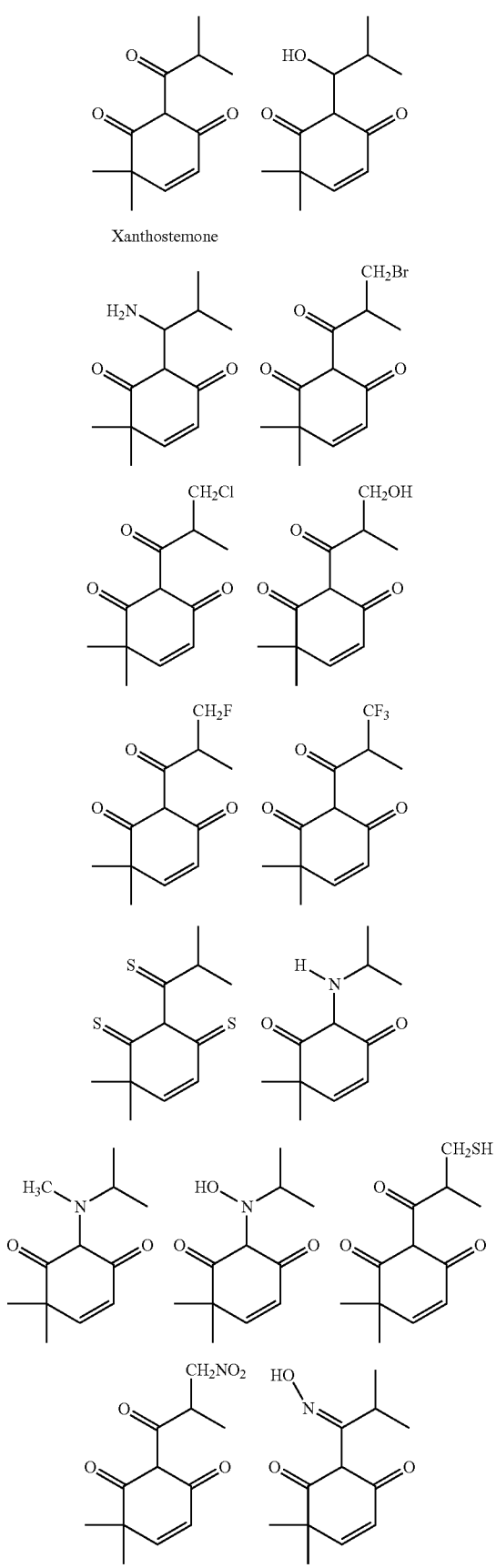

Xanthostemone

Derivatives of the above compounds include, but are not restricted to, ethoxylate derivatives, propoxylate derivatives, hydrates, aldehyde derivatives, ester derivatives, ether derivatives, alcohol derivatives, phenol derivatives, amine derivatives, other biologically or chemically equivalent substances, and any combination of two or more of the foregoing.

Similarly effective as pesticides are salts of the above compounds, including mono-valent salts (e.g., sodium, potassium) and di-valent metal salts (e.g., calcium, magnesium, iron or copper) and ammonium salts (e.g., isopropyl ammonium, trialkyl and tetraalkylammonium salts).

The compounds according to any one of formulae (I)-(V) can be prepared according to methods analogous to those known in the art for the preparation of β-diones. Exemplary methods are disclosed for example in EP-A-338992, EP-A-336898, U.S. Pat. No. 4,202,840, U.S. Pat. No. 4,869,748, EP-A-186118, EP-A-186119, EP-A-186120, U.S. Pat. No. 4,695,673, U.S. Pat. No. 4,780,127, U.S. Pat. No. 4,921,526, U.S. Pat. No. 5,006,150, U.S. Pat. No. 5,545,607, U.S. Pat. No. 5,925,795, U.S. Pat. No. 5,990,046, U.S. Pat. No. 6,218,579, EP-A-249150, EP-A-137963, EP-A-394889 EP-A-506907 or EP-B-135191.

More particularly, compounds according to formulae (III)-(V) can be synthesised using the representative procedures outlined below.

For compounds according to formula (III), 1,3,5-trihydroxybenzene 1 is reacted with $CH_3CN$ in the presence of zinc chloride and hydrochloric acid, according to A. H. Blatt (1943, *Org. Synth. Col.* II, 522-523), affording 1-acetyl-2,4,6-trihydroxybenzene 2 (phloroacetophenone) (R=Me) (Scheme 1).

Scheme 1

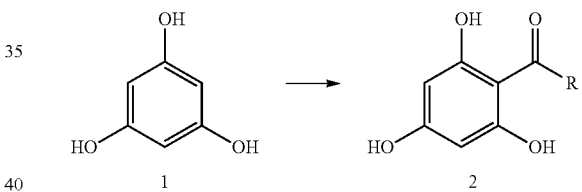

R groups other than methyl are depicted above. Reaction of 1-acetyl-2,4,6-trihydroxybenzene 2 affording 1-acetyl-3,3,5,5-tetramethylcyclohexan-2,4,6-trione 3 is a representative procedure for all compounds according to formula (III) (R. A. Gray et al., U.S. Pat. No. 4,202,840) (Scheme 2). Anhydrous MeI (6 eq) is slowly added, at room temperature under an atmosphere of nitrogen, to a mechanically stirred solution of 1-acetyl-2,4,6-trihydroxybenzene 2 (1 eq) and sodium ethoxide (6 eq) in anhydrous methanol. The mixture is refluxed for 4 hours. On cooling the mixture is concentrated under vacuo, providing a residue, which is diluted with water and acidified with 2 M hydrochloric acid. Diethylether extracts are washed with saturated sodium sulfite solution, water and then dried ($Na_2SO_4$). Evaporation of the diethylether provides the desired product 3.

Scheme 2

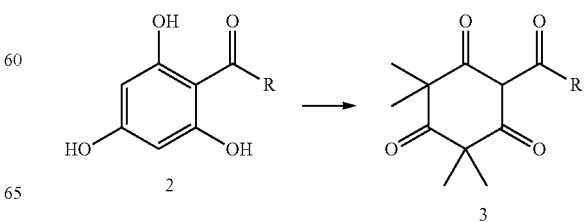

For mono, di, tri and tetra B, C, D, E, F substitution patterns, reactions between one and seven mole equivalents of R-I and sodium ethoxide are used. Lawasson's reagent is used for conversion of oxygen into sulfur groups and sodium borohydride or sodium cyanoborohydride is used to reduce ketone, thioketone and imino groups. When additional carbonyl groups are introduced into the cyclohexane ring system the procedure of Crow is utilised (M. L. Bolte et al., 1985, *Agric. Biol. Chem.*, 49, 761).

Compounds of formula (IV) can be prepared according to a first representative procedure, as follows: 3-methoxy-2,4,4-trimethylcyclohex-2-en-1,5-dione 4 (1 mole eq), prepared according to Herzig (J. Herzig, and F. Wenzel, *Monatsh*, 1903, 24, 101), is dissolved in anhydrous diethylether and hexamethylphosphoramide (solvent ratio, 20:1 respectively) under an atmosphere of nitrogen. The mixture is cooled to 0° C. and lithium hydride (1.1 mole eq) (60% in mineral oil) is added in portions. After addition the mixture is stirred for a further 10 mins before the addition of benzoyl cyanide 5 [R—CO—CN, R is depicted above] (1.1 mole eq). The mixture is allowed to warm to room temperature over 12 h at which time the reaction is quenched with water and partitioned. The ether layer is dried ($Na_2SO_4$) and evaporated affording crude 1-benzoyl-3-methoxy-2,4,4-trimethyl-cyclohex-2-en-1,5-dione 6 which is purified by $SiO_2$ column chromatography (hexane/ethyl acetate, gradient) (Scheme 3).

Scheme 3

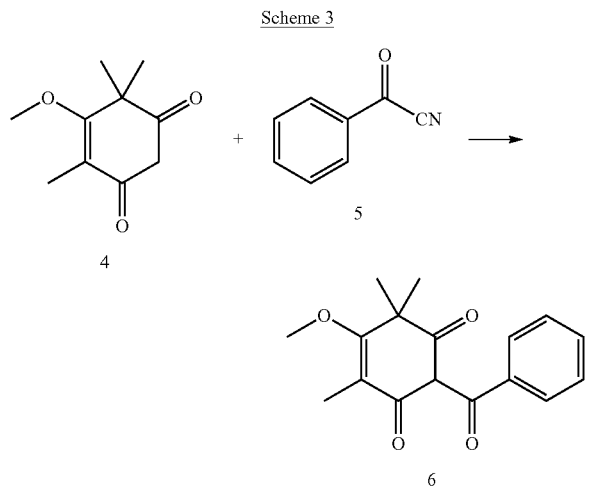

Alternatively, compounds of formula (IV) can be prepared according to a second representative procedure, as follows: 3-methoxy-2,4,4-trimethylcyclohex-2-en-1,5-dione 4 (1 mole eq) (commercially available) and benzoyl cyanide are dissolved in anhydrous dichloromethane and cooled to 0° C. under an atmosphere of nitrogen. To the cooled solution is added anhydrous finely powdered zinc chloride (1.1 mole eq.) followed by slow addition of triethylamine (1.2 mole eq). The reaction mixture is stirred at room temperature for 5-6 h and then poured into 2 M hydrochloric acid. The mixture is partitioned and the dichloromethane layer is washed with 5% sodium carbonate. The aqueous carbonate phase is then acidified with hydrochloric acid and extracted with methylene chloride and dried ($Na_2SO_4$). The solvent is removed and the residue subjected to $SiO_2$ column chromatography (hexane/ethyl acetate) affording 1-benzoyl-3-methoxy-2,4,4-trimethylcyclohex-2-en-1,5-dione 6 (W. J. Michaely and G. W. Kraatz, EP-B-135191).

Compounds of formula (V) can be prepared according to a first representative procedure, as follows: 4,4-dimethylcy-clohexane-1,3-dione 7 (1 mole eq) (commercially available) is dissolved in anhydrous diethylether and hexamethylphosphoramide (solvent ratio, 20:1 respectively) under an atmosphere of nitrogen. The mixture is cooled to 0° C. and lithium diisopropylamide (2.1 mole eq) is added dropwise over 40 mins. The mixture is then stirred for a further 10 mins before the addition of methyl iodide (1 mole eq). The mixture is stirred for 12 h and then benzoyl cyanide (2 mole eq) is added and the mixture stirred for a further 24 h. The reaction was quenched with water and the ether layer partitioned and dried ($Na_2SO_4$). The solvent was removed and the residue subjected to $SiO_2$ column chromatography (hexane/ethyl acetate) affording 1-benzoyl-3,3,5-trimethyl-cyclohexan-2,6-dione 8 (Scheme 4).

Scheme 4

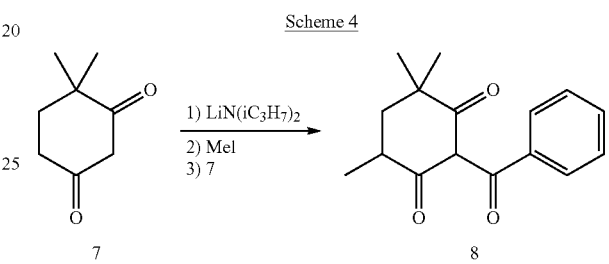

Alternatively, the compounds of formula (V) can be prepared according to a second representative procedure, as follows: 4,4-dimethyl-1,3-cyclohexanedione 7 (1 mole eq) (commercially available) and benzoyl cyanide are dissolved in anhydrous dichloromethane and cooled to 0° C. under an atmosphere of nitrogen. To the cooled solution is added anhydrous finely powdered zinc chloride (1.1 mole eq) followed by slow addition of triethylamine (1.2 mole eq). The reaction mixture is stirred at room temperature for 5-6 h and then poured into 2 M hydrochloric acid. The mixture is partitioned and the dichloromethane layer washed with 5% sodium carbonate. The aqueous carbonate phase is then acidified with hydrochloric acid and extracted with methylene chloride and dried ($Na_2SO_4$). The solvent is removed and the residue subjected to $SiO_2$ column chromatography (hexane/ethyl acetate) affording 1-benzoyl-3,3,5-trimethyl-cyclohexan-2,6-dione 8. (W. J. Michaely and G. W. Kraatz, EP-B-135191).

Dehydroangustione and xanthostemone derivatives are simply derived from dehydrogenation of angustione derivatives, for example, by treatment of 1-benzoyl-3,3,5-trimethylcyclohexan-2,6-dione 8 with palladium on charcoal in methanol, which thereby affords 1-benzoyl-3,5,5-trimethylcyclohex-3-en-2,6-dione 9 (Scheme 5).

Scheme 5

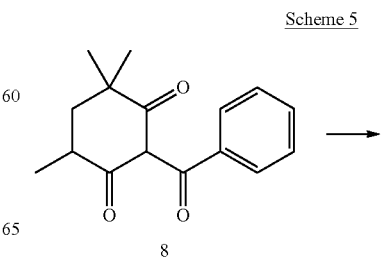

-continued

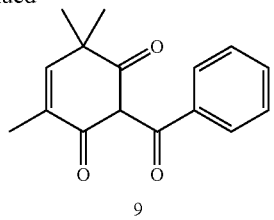

9

Metal salts (enolates) of the above compounds can be prepared by the reaction of triketone derivatives with the corresponding metal hydroxides suspended in methanol or ethanol. Trialkylammonium salts can be prepared by the reaction of triketone derivatives (e.g., 3) with trialkylamines in a chlorinated solvent such as dichloromethane. Tetraalkylammonium salts can be prepared by adding a halogenated tetraalkylammonium salt to a metal salt in dichloromethane, which precipitates the metal halide removed by filtration. The pure material is obtained by evaporation of the filtrate.

The present inventors have discovered that the β-diones of the invention can be obtained from natural sources and, in particular, from volatile oil-bearing organisms. Accordingly, in another aspect, the present invention encompasses the use of a β-dione compound, particularly a β-diketone or a β-triketone compound, obtainable from a volatile oil-bearing organism, including an analogue or derivative thereof, in the preparation of a pesticidal composition for controlling harmful, annoying or undesired pests.

The present invention contemplates the use of any volatile oil-bearing organism that produces β-diones, preferably the β-diones according to any one of formulae (I)-(V), and especially β-diketones and/or β-triketones, for the preparation of the pesticidal compositions of the invention. Preferred volatile oil-bearing organisms are volatile oil-bearing plants including, but not restricted to, plants from the families Alliaceae, Apiaceae, Asteraceae, Cannabinaceae, Lamiaceae, Pteridaceae, Myrtaceae, Myoporaceae, Proteaceae, Rutaceae and Zingiberaceae. Preferably, the volatile oil-bearing plant is selected from genera of the Myrtaceae family including, but not limited to, *Angophora, Austromyrtus, Backhousia, Baeckea, Callistemon, Corymbia, Danvinia, Eucalyptus, Kunzea, Leptospermum, Melaleuca, Syzygium* and *Xanthostemon*.

Thus, the compositions of the present invention may contain as active ingredients substantially purified β-diones or crude β-dione-containing extracts obtained from a volatile oil-bearing organism, preferably a volatile oil-bearing plant. Volatile oils, also known in the art as essential oils, typically comprise a volatile mixture of esters, aldehydes, alcohols, ketones and terpenes, which can be prepared from botanical materials or plant cell biomass from cell culture. Volatile oils can be prepared by subjecting botanical materials to a distillation process, for example. A number of different procedures can be used for distillation. For example, plant matter (e.g., foliage, stems, roots, seeds, bark etc) of a volatile oil-bearing plant is placed in a suitable still and steam distillation is used to break down the cells of the plant to release the oil. The steam is then condensed and the oil phase is separated from the aqueous phase to obtain the volatile oil. It will be appreciated that other methods of volatile oil extraction (e.g., solvent extraction) are known to those of skill in the art and it will be understood, in this regard, that the present invention is not limited to the use or practice of any one particular method of extracting volatile oils.

Suitably, the compositions comprise naturally-occurring compounds derived from a volatile oil-bearing organism. Thus, in a preferred embodiment, the pesticidal composition of the invention comprises one or more β-dione active compounds, particularly β-diketone- and/or β-triketone-active compounds, that are derived from the volatile oil of a volatile oil-bearing organism. In this embodiment, the composition may optionally contain a naturally-occurring carrier and/or other naturally-occurring additives.

Naturally-occurring additives contemplated by the present invention include natural antioxidants, which can be used advantageously to reduce the effect of oxidation of the compounds of the invention. An example of a suitable naturally-occurring antioxidant is α-tocopherol. Other additives, such as naturally-occurring stabilisers, are also contemplated, which may desirably be added to improve the stability and shelf life of the composition. Examples of suitable natural stabilisers include gum arabic, guar gum, sodium caseinate, polyvinyl alcohol, locust bean gum, xanthan gum, kelgum, and mixtures thereof.

In an alternate embodiment, the naturally-occurring compounds derived from a volatile oil may be modified or derivatised to improve, for instance, their shelf-life, stability, activity and/or bioavailability.

The compounds of the present invention are useful for controlling harmful, annoying or undesired pests. They may be used singularly or in combination with other pest-controlling compounds of the invention. By "controlling" is meant preventing, combating, eradicating, destroying, repelling, or mitigating pests or increasing the mortality or inhibiting the growth and/or development of pests. The term "pest" is used herein in its broadest sense and includes within its scope insects, arachnids (e.g., acari, spiders), helminths (e.g., nematodes), molluscs, protozoa (e.g., *Plasmodium* sp. *Paramecium* sp.), viruses (e.g., herpesviruses) and the like. Suitable applications for such control include, but are not limited to, combating and/or eradicating infestations by pests in animals (including humans) and/or plants (including trees) and/or stored products, which includes the administration to the animal or site of an effective quantity of a compound of the invention.

By "effective amount" is meant the administration or application of that amount of active compound, either in a single dose or as part of a series, that is effective for controlling a significant number of pests. Thus, for example, a "pesticidally-effective" amount is the amount of active compound that is effective for increasing the mortality or decreasing the growth of a significant number of pests. Alternatively, a "pest-repelling" effective amount is the amount of active compound that is noxious to, and/or induces behavioural changes in, a significant number of pests. The effective amount will vary depending upon the taxonomic group of pest exposed to the active compound, the formulation of the composition, and other relevant factors. It is expected that the amount will fall in a relatively broad range that can be determined through routine trials.

Accordingly, the compounds of the present invention can be used as pesticides, such as but not limited to insecticides, arachnicides, anti-helminthics, molluscicides antivirals, antiprotozoals and the like, or as pest repellents including repellents of insects, arachnids, helminths, molluscs, protozoa and viruses. In especially preferred embodiments, the compounds of the present invention are used in the control of insects, arachnids, helminths or molluscs. In practice, the compounds can be applied as formulations containing the various adjuvants and carriers known to or used in the industry for facilitating bioavailability, stability and dispersion. The choice of formulation and mode of application for any given compound may affect its activity, and selection will be made accordingly.

In general, a pest-controlling compound of the invention can be compounded with appropriate inert carriers and additives in an appropriate ratio by means of dissolving, separating, suspending, mixing, impregnating, adsorbing or precipitating operation to formulate into oil formulations, emulsifiable concentrates, wettable powders, flowables, granules, powders, dusts, solutions, suspensions, emulsions, controlled-release forms such as microcapsules, aerosols or fumigants. Typically, the compounds of the present invention can be mixed with a solid carrier, liquid carrier or gas carrier, optionally together with a surfactant and other adjuvants useful for such formulations.

The compounds of the invention can be used in an amount from about 0.00005% to about 90% by weight as contained in these formulations as their active component. As used herein, the term "about" refers to a quantity, level, value or amount that varies by as much as 30%, preferably by as much as 20%, and more preferably by as much as 10% to a reference quantity, level, value or amount.

Where the compounds are in the form of β-dione-containing extracts, the formulations will usually comprise as their principal active ingredient from about 0.0001% to about 90%, preferably from about 0.0001% to about 50%, more preferably from about 0.0005% to about 10%, even more preferably from about 0.0005% to about 5%, even more preferably from about 0.0005% to about 1% and still even more preferably from about 0.001% to about 0.5% by weight of the extract.

Alternatively, where the compounds are in the form of substantially purified preparation of β-diones, the formulations will usually comprise as their principal active ingredient from about 0.00005% to about 90%, preferably from about 0.0001% to about 50%, more preferably from about 0.0005% to about 10%, even more preferably from about 0.001% to about 5% and still even more preferably from about 0.001% to about 1% by weight of the substantially purified β-dione.

By "substantially purified" is meant a compound which has been separated from components that naturally accompany it. Typically, a compound is substantially pure when at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., by chromatography or HPLC analysis.

Examples of solid carriers useful in preparing the formulations are clays including kaolin clay, diatomite, water-containing synthetic silicon oxide, bentonite, Fubasami clay, and acid clay; talcs; ceramics; inorganic minerals such as Celite, quartz, sulfur, active carbon, calcium carbonate and hydrated silica; and chemical fertilisers such as ammonium sulfate, ammonium phosphate, ammonium nitrate, urea and ammonium chloride, these solid carriers being finely divided or granular. Examples of useful liquid carriers are water, alcohols such as methanol and ethanol, ketones such as acetone and methyl ethyl ketone, aromatic hydrocarbons such as benzene, toluene, xylene, ethylbenzene and methylnaphthalene, aliphatic hydrocarbons such as hexane, cyclohexane, kerosene and light oil, esters such as ethyl acetate and butyl acetate, nitriles such as acetonitrile and isobutyronitrile, ethers such as diisopropyl and dioxane, acid amides such as N,N-dimethylformamide and N,N-dimethylacetamide, halogenated hydrocarbons such as dichloromethane, trichloroethane and carbon tetrachloride, dimethyl sulfoxide, and fish oils, mineral oils, plant derived oils such as canola oil, cotton-seed oil, soybean oil and sesame oil as well as essential oils such as lavender oil, *eucalyptus* oil, tea tree oil, *citrus* oil etc. Solid or liquid carriers can be used alone or in combination. Examples of gas carriers, i.e., those of propellants, are butane gas, LPG (liquefied petroleum gas), dimethyl ether, fluorocarbons and carbon dioxide gas.

Examples of surfactants are alkylsulfuric acid esters, alkylsulfonic acid salts, alkylarylsulfonic acid salts, alkyl aryl ethers and polyoxyethylene adducts thereof, polyethylene glycol ethers, polyhydric alcohol esters, sugar alcohol derivatives, sorbitane monolaurate, alkylallyl sorbitane monolaurate, alkylbenzene sulfonate, alkylnaphthalene sulfonate, lignin sulfonate, and sulfuric acid ester salts of higher alcohols. These surfactants may be used alone or in combination.

Examples of adjuvants for the formulations, such as binders and dispersants, are casein, gelatin, polysaccharides such as starch, gum arabic, cellulose derivatives and alginic acid, lignin derivatives, bentonite, sugars and water-soluble synthetic high-molecular-weight substances such as polyvinyl alcohol, polyvinyl pyrrolidone and polyacrylic acids. Examples of stabilisers are PAP (acid isopropyl phosphate), BHT (2,6-di-tert-butyl-4-methylphenol), BHA (mixture of 2-tert-butyl-4-methoxyphenol and 3-tert-butyl-4-methoxyphenol), synergists such as piperonyl butoxide, vegetable oils, mineral oils, fish oils, surfactants and fatty acids or esters thereof.

Emulsifying agents that may be used are suitably one or more of those selected from non-ionic or anionic emulsifying agents. Examples of non-ionic emulsifying agents include, but are not restricted to, polyoxyethylenealkylphenylether, polyoxyethylenealkylether, polyethyleneglycol fatty ester, sorbitan fatty ester, polyoxyethylene sorbitan fatty ester, polyoxyethylenesorbitol fatty ester, polyoxyethylenepolyoxypropylenealkylether. Examples of anionic emulsifying agents include alkyl sulphates, polyoxyethylenealkylether sulphates, sulfosuccinates, taurine derivatives, sarcosine derivatives, phosphoric esters, alkylbenzenesulfonates and the like. A mixture consisting of polyoxyethylenestyrylphenylether and calcium allylbenzenesulfonate is preferred. These emulsifying agents may be used in an amount of 5 to 20 weight parts per 100 weight parts of the compositions of the present invention.

Formulation thus obtained can be used solus or diluted, for example, with water or other diluent. The formulations can be used also as admixtures with other pesticides such as insecticides, arachnids, anti-helminthics, molluscicides, herbicides, plant growth regulators, synergists, soil improvers, baits and the like, or can be used simultaneously with such agents without mixing. For example, the pest-controlling compounds of the invention can be combined with other naturally derived bioactive compounds or extracts such as neem or its components, derris, pyrethrum; microbial extracts such as avermectins or streptomycins; with synthetic insecticides, acaricides, molluscicides, anti-helminthics; anti-protozoals, antivirals or with microorganisms having insecticidal, acaricidal, molluscicidal, anti-helminthic anti-protozoal or antiviral activity e.g., bacteria such as *Bacillus thuringiensis, Bacillus popillae*, entomogenous fungi such as *Metarhizium* spp., *Verticillium lecanii*, nematodes such as *Steinernema* spp and *Heterorhabditis*. Alternatively, or in addition, the pest-controlling compounds of the invention can be combined with synergists such as piperonyl butoxide, and with ultraviolet screening compounds of natural or synthetic origin.

When used as an agricultural pesticide, the compound of the invention is preferably applied usually in an amount of 0.01 to 500 g/100 m². When an emulsifiable concentrate, wettable powder or flowables are used as diluted with water, the compound is applied usually at a concentration of 0.1 to 1000 ppm, preferably 1 to 500 ppm. The granular or dust can be applied without dilution.

The amount or concentration of application, although exemplified above, can be suitably increased or reduced according to the type of preparation, time, place, method of application, kind of pest and extent of harm or annoyance suffered.

The invention also contemplates the use of the above described β-dione compounds in pest repellent, particularly insect repellent, compositions. Repellent compositions contemplated by the present invention include those that are noxious to, and/or induce behavioural changes in, a pest. The latter compositions suitably comprise an activity including, but not restricted to, an antifeedant activity, an oviposition deterrent activity and an insect growth regulatory activity. Insect repellent compositions in various dosage forms can be prepared by blending the above-described β-dione compounds as active ingredients with a base of cosmetics or pharmaceuticals, which are usually applied to human bodies or animals. They can be formulated in, for example, lotions, aerosols, milky lotions, creams or the like. These compounds can be further incorporated with other insect repellents, antioxidants, UV-absorbers, humectants or other additives.

The above compounds or the above-prepared compositions of the present invention can be applied directly to human bodies or animals. Besides, substrates, such as sheets, films, nets, timber or the like, which have preliminarily been treated with the above compounds or compositions by means of application, impregnation or blending, can also be used.

The quantity of the above compounds to be formulated in the noxious-insect repellents depends upon the dosage form, usage or other conditions. Suitable dosages may be selected from about 0.1% to about 90% by weight.

Thus, in another aspect of the present invention there is provided a method for controlling harmful, annoying or undesired pests, said method comprising exposing said pests to a pest-controlling effective amount of a composition comprising a β-dione compound as broadly described above. Preferred embodiments of this type include exposing said pests to a pesticidally effective amount or a pest-repelling effective amount of said composition.

The terms "comprise", "comprises" and "comprising" and the like refer, unless the context requires otherwise, to the inclusion of a stated step or element or group of steps or elements but not the exclusion of any other step or element or group of steps or elements.

The compositions and methods of the present invention may be applied to pests including, but not restricted to, insects, arachnids, helminths, molluscs, protozoa and viruses. For example, suitable insects that fall within the scope of the present invention include those:

(a) from the order of the lepidopterans (Lepidoptera), for example, *Adoxophyes orana, Agrotis ypsilon, Agrotis segetum, Alabama argillacea, Anticarsia gemmatalis, Argyresthia conjugella, Autographa gamma, Cacoecia murinana, Capua reticulana, Choristoneura fumiferana, Chilo partellus, Choristoneura occidentalis, Cirphis unipuncta, Cnaphalocrocis medinalis, Crocidolomia binotalis, Cydia pomonella, Dendrolimus pini, Diaphania nitidalis, Diatraea grandiosella, Earias insulana, Elasmopalpus lignosellus, Eupoecilia ambiguella, Feltia subterranea, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera scitella, Lithocolletis blancardella, Lobesia botrana, Loxostege sticticalis, Lymantria dispar, Lymantria monacha, Lyonetia clerkella, Manduca sexta, Malacosoma neustria, Mamestra brassicae, Mocis repanda, Operophthera brumata, Orgyia pseudotsugata, Ostrinia nubilalis, Pandemis heparana, Panolis flammea, Pectinophora gossypiella, Phthorimaea operculella, Phyllocnistis citrella, Pieris brassicae, Plathypena scabra, Platynota stultana, Plutella xylostella, Prays citri, Prays oleae, Prodenia sunia, Prodenia ornithogalli, Pseudoplusia includens, Rhyacionia frustrana, Scrobipalpula absoluta, Sesamia inferens, Sparganothis pilleriana, Spodoptera frugiperda, Spodoptera littoralis, Spodoptera litura, Syllepta derogata, Synanthedon myopaeformis, Thaumatopoea pityocampa, Tortrix viridana, Trichoplusia ni, Tryporyza incertulas, Zeiraphera canadensis,*

(b) furthermore *Galleria mellonella* and *Sitotroga cerealella, Ephestia cautella, Tineola bisselliella;*

(c) from the order of the beetles (Coleoptera), for example, *Anthonomus grandis, Anthonomus pomorum, Apion vorax, Atomaria linearis, Blastophagus piniperda, Cassida nebulosa, Cerotoma trifurcata, Ceuthorhynchus assimilis, Ceuthorhynchus napi, Chaetocnema tibialis, Conoderus vespertinus, Crioceris asparagi, Dendroctonus refipennis, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllopertha horticola, Phyllophaga sp., Phyllotreta chrysocephala, Phyllotreta nemorum, Phyllotreta striolata, Popillia japonica, Psylliodes napi, Scolytus intricatus, Sitona lineatus,*

(d) furthermore *Bruchus rufimanus, Bruchus pisorum, Bruchus lentis, Sitophilus granaria, Lasioderma serricorne, Oryzaephilus surinamensis, Rhyzopertha dominica, Sitophilus oryzae, Tribolium castaneum, Trogoderma granarium, Zabrotes subfasciatus;*

(e) from the order of the dipterans (Diptera), for example, *Anastrepha ludens, Ceratitis capitata, Contarinia sorghicola, Dacus cucurbitae, Dacus oleae, Dasineura brassicae, Delia coarctata, Delia radicum, Hydrellia griseola, Hylemyia platura, Liriomyza sativae, Liriomyza trifolii, Mayetiola destructor, Orseolia oryzae, Oscinella frit, Pegomya hyoscyami, Phorbia antiqua, Phorbia brassicae, Phorbia coarctata, Rhagoletis cerasi, Rhagoletis pomonella,*

(f) furthermore *Aedes aegypti, Aedes vexans, Anopheles maculipennis, Chrysomya bezziana, Chrysomya hominivorax, Chrysomya macellaria, Cordylobia anthropophaga, Culex pipiens, Fannia canicularis, Gasterophilus intestinalis, Glossina morsitans, Haematobia irritans, Haplodiplosis equestris, Hypoderma lineata, Lucilia caprina, Lucilia cuprina, Lucilia sericata, Musca domestica, Muscina stabulans, Oestrus ovis, Tabanus bovinus, Simulium damnosum;*

(g) from the order of the *thrips* (Thysanoptera), for example, *Frankliniella fusca, Frankliniella occidentalis,*

*Frankliniella tritici, Haplothrips tritici, Heliothrips haemorrhoidalis, Scirtothrips citri, Thrips oryzae, Thrips palmi, Thrips tabaci;*

(h) from the order of the hymenopterans (Hymenoptera), for example, *Athalia rosae, Atta cephalotes, Atta sexdens, Atta texana, Hoplocampa minuta, Hoplocampa testudinea, Iridomyrmes humilis, Iridomyrmex purpureus, Monomorium pharaonis, Solenopsis geminata, Solenopsis invicta, Solenopsis richteri, Technomyrmex albipes;*

(i) from the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus hesperus, Lygus lineolaris, Lygus pratensis, Nezara viridula, Piesma quadrata, Solubea insularis, Thyanta perditor;*

(j) from the order of the homopterans (Homoptera), for example, *Acyrthosiphon onobrychis, Acyrthosiphon pisum, Adelges laricis, Aonidiella aurantii, Aphidula nasturtii, Aphis fabae, Aphis gossypii, Aphis pomi, Aulacorthum solani, Bemisia tabaci, Brachycaudus cardui, Brevicoryne brassicae, Dalbulus maidis, Dreyfusia nordmannianae, Dreyfusia piceae, Dysaphis radicola, Empoasca fabae, Eriosoma lanigerum, Laodelphax striatella, Macrosiphum avenae, Macrosiphum euphorbiae, Macrosiphon rosae, Megoura viciae, Metopolophium dirhodum, Myzus persicae, Myzus cerasi, Nephotettix cincticeps, Nilaparvata lugens, Perkinsiella saccharicida, Phorodon humuli, Psylla mali, Psylla pini, Psylla pyricola, Rhopalosiphum maidis, Schizaphis graminum, Sitobion avenae, Sogatella funcifera, Toxoptera citricida, Trialeurodes abutilonea, Trialeurodes vaporariorum, Viteus vitifolii;*

(k) from the order of the termites (Isoptera), for example, *Calotenmes flavicollis, Coptotenmes spp, Leucotenmes flavipes, Macnotenmes subhyalinus, Nasutitermes spp* such as *Nasutitermes walkeri, Odontotenmes fonmosanus, Reticulitermes lucifugus, Tenmes natalensis;*

(l) from the order of the orthopterans (Orthoptera), for example, *Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Schistocerca americana, Schistocerca peregrina, Stauronotus manoccanus, Schistocerca gregaria,*

(m) furthermore *Acheta domestica, Blatta orientalis, Blattella germanica, Periplaneta americana;*

(n) from the order of the phthirapterans (Phthiraptera), for example, *Mallophaga,* such as *Damalina* spp., and Anoplura such as *Linognathus* and *Haematopinus* spp.;

(o) from the order of the hemipterans (Hemiptera), for example, *Aphis, Bemisia, Phorodon, Aeneolamia, Empoasca, Parkinsiella, Pyrilla, Aonidiella, Coccus, Pseudococcus, Helopeltis, Lygus, Dysdencus, Oxycanenus, Nezara, Aleyrodes, Triatoma, Psylla, Myzus, Megoura, Phylloxera, Adelges, Nilaparvata, Nephotettix* or *Cimwx* spp.;

(p) from the order of the siphonapterans (Siphonaptera), for example, *Ctenocephalides* or *Pulex* spp.;

(q) from the order of the thysanurans (Thysanura), for example, *Lepisma* spp.;

(r) from the order of the dermapterans (Dermaptera), for example, *Forficula* spp.; and (s) from the order of the psocopterans (Psocoptera), for example, *Peripsocus* spp.

Arachnids contemplated by the present invention include, but are not limited to, spiders and scorpions and especially mites such as phytophagous mites (Acari), such as *Aculops lycopersicae, Aculops pelekassi, Aculus schlechtendali, Brevipalpus phoenicis, Bryobia praetiosa, Eotetranychus carpini, Eutetranychus banksii, Eriophyes sheldoni, Oligonychus pratensis, Panonychus ulmi, Panonychus citri, Phyllocoptruta oleivora, Polyphagotarsonemus latus, Tarsonemus pallidus, Tetranychus cinnabarimus, Tetranychus kanzawai, Tetranchus pacificus, Tetranychus urticae,* ticks, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Rhipicephalus appendiculatus* and *Rhipicephalus evertsi,* and animal-parasitic mites, such as *Dermanyssus gallinae, Psoroptes ovis* and *Sarcoptes scabiei.*

Helminths falling within the scope of the present invention may be selected from cestodes such as fish tapeworm, pork tapeworm, beef tapeworm, and dwarf tapeworm; trematodes such as from the genera *Metagonimus* and *Heterophyes*; and nematodes such as but not limited to filariid, ascarid, strongyle and trichostrongyle nematodes of the genera *Acanthocheilonema, Aelurostrongylus, Ancylostoma, Angiostrongylus, Ascaris, Brugia, Bunostomum, Dictyocaulus, Dioctophyme, Dipetalonema, Dirofilaria, Dracunculus, Filaroides, Lagochilascaris, Loa, Mansonella, Muellerius, Necator, Onchocerca, Parafilaria, Parascaris, Protostrongylus, Setaria, Stephanofilaria, Strongyloides, Strongylus, Thelazia, Toxascaris, Toxocara, Trichinella, Uncinaria* and *Wuchereria.*

Suitable molluscs include those of the Gastropoda class examples of which include snails, slugs, conchs, and whelks.

Protozoa may be selected for example from *Plasmodia, Toxoplasma, Leishmania, Trypanosoma, Giardia, Entamoeba, Acanthamoeba, Nagleria, Hartmanella, Balantidium, Babesia, Cryptosporidium, Isospora, Microsporidium, Trichomonas* or *Pneumocystis* species.

Viruses may be selected from RNA viruses or DNA viruses, which include but are not limited to Human Immunodeficiency Virus (HIV), Poliovirus, Influenza virus, Rous Sarcoma virus, Flaviviruses such as Japanese encephalitis, Influenza virus, Respiratory Syncytial Virus, Hepatitis virus, Parvovirus, Rotavirus, Coronavirus, Adenovirus and Herpesviruses such as Papillomavirus and Epstein-Barr virus.

The present invention also extends to methods for producing resistance in plants to pests including, but not limited to, insects, arachnids, helminths, molluscs, protozoa and viruses by crossing a plant expressing a β-dione compound according to the invention with pest susceptible lines. Crossing a β-dione-producing plant into a pest susceptible background would produce a resistant plant with a high level of pest resistance. Plants that could be made pest resistant include, but are not limited to, dicotyledonous plants, especially trees and more especially members of the Myrtaceae family. For example *E. cloeziana* commonly known as Gympie Messmate is one of the many *Eucalyptus* species grown for hard wood production. However the oil present in this chemotype does not contain β-diones and hence an intra species cross with the unique North Queensland tasmanone chemotype would introduce this phenotypic trait. Such a process would be readily applicable to other *Eucalyptus* species of commercial interest. Interspecific crossing within the Myrtaceae family is well established to those skilled in the art and inclusion of β-dione as an additional trait into formal breeding programs is acknowledged.

Suitable β-dione-producing plants may be selected from the families Alliaceae, Apiaceae, Asteraceae, Cannabinaceae, Lamiaceae, Pteridaceae, Myrtaceae, Myoporaceae, Proteaceae, Rutaceae and Zingiberaceae. Preferably, the volatile oil-bearing plant is selected from genera of the Myrtaceae family including, but not limited to, *Angophora, Austromyrtus, Backhousia, Baeckea, Callistemon, Corymbia, Danvinia, Eucalyptus, Kunzea, Leptospermum, Melaleuca, Syzygium* and *Xanthostemon*. Preferred β-dione-producing plants are *Leptospermum morrisonii, Eucalyptus bensonii, Eucalyptus megacornuta, Eucalyptus pilularis, Eucalyptus cornuta, Eucalyptus baxteri, Eucalyptus macrorhyncha, Eucalyptus cloeziana, Melaleuca cajuputi, Eucalyptus jensenii, Backhousia angustifolia* and *Leptospermum scoparium*. A particularly preferred β-dione-producing plant is *Eucalyptus cloeziana*.

As used herein, the term "plant" includes reference to whole plants, plant organs (e.g., leaves, stems, roots, etc.), seeds and plant cells and progeny of same. Plant cell, as used herein includes, without limitation, seeds suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants.

Thus, the present invention contemplates conventional plant breeding methods to transfer the genetic material associated with β-dione production via crossing and backcrossing. Such methods will comprise the steps of: (1) sexually crossing the β-dione-producing plant with a plant from a pest susceptible taxon; (2) recovering reproductive material from the progeny of the cross; and (3) growing β-dione-producing/pest-resistant plants from the reproductive material. Where desirable or necessary, the agronomic characteristics of the susceptible taxon can be substantially preserved by expanding this method to include the further steps of repetitively: (1) backcrossing the pest-resistant progeny with pest-susceptible plants from the susceptible taxon; and (2) selecting for expression of a β-dione (or an associated marker gene) among the progeny of the backcross, until the desired percentage of the characteristics of the susceptible taxon are present in the progeny along with the gene or genes imparting β-dione activity.

By the term "taxon" herein is meant a unit of botanical classification. It thus includes, genus, species, cultivars, varieties, variants and other minor taxonomic groups which lack a consistent nomenclature.

In order that the invention may be readily understood and put into practical effect, particular preferred embodiments will now be described by way of the following non-limiting examples.

EXAMPLES

Example 1

β-Triketone-Containing Oils Obtained from Australian Myrtaceae Species

Australia has an extensive number of volatile oils from species of the Myrtaceae that are rich in a diversity of structurally related constituents known as β-triketones. These oils often show not only a high yield of oil, but also a high degree of biosynthetic selectivity that produces β-triketones in a high proportion of the oil composition. The major constituents of the published Myrtaceae essential oils (Hellyer, 1968; Boland and Brophy, 1990, 1993; Brophy, et al., 1995; Bignall et al., 1997; Southwell and Brophy 2000) are listed in Table 1 and their structures are included in FIG. 1.

TABLE 1

β-Triketone Profiles of Australian Essential Oils

| Species | Yield | β-Triketone (%) | Distribn |
|---|---|---|---|
| *Backhousia angustifolia* | 2.5 | Angustione (85) | QLD |
| *Backhousia angustifolia* | 2.5 | Dehyroangustione (80) | QLD |
| *Eucalyptus cloeziana* | 3.0 | Tasmanone (95) | QLD |
| *Eucalyptus suberea* | 1.4 | Tasmanone (94) | WA |
| *Eucalyptus lateritica* | 0.9 | Tasmanone (37), laterticone (14) | WA |
| *Eucalyptus camfieldii* | | Tasmanone (40) | NSW |
| *Leptospermum scoparium* | 0.4 | Leptospermone (19), Flavesone (8), Isoleptospermone (5) | NSW, NZ |
| *Eucalyptus grandis* | 0.6 | Leptospermone (20), Flavesone (13), Isoleptospermone (3) | NSW |
| *Eucalyptus agglomerata* | | Agglomerone (40) | NSW |
| *Eucalyptus mckieana* | | Agglomerone (60) | NSW |
| *Eucalyptus bensonii* | 2.5 | Agglomerone (72) | |
| *Eucalyptus insularis* | 1 | Agglomerone (19) | WA |
| *Eucalyptus jensenii* | 0.3 | Jensenone (70) | NT |
| *Eucalyptus papuana* | 0.7 | Papuanone (40) | Nth Aus |
| *Leptospermum morrisonii* | 1.8 | Grandiflorone (58) | NSW |
| *Melaleuca cajeputi* | | Platyphyllol | Nth Aus |
| *Xanthostemon oppositifolius* | | Xanthostemone | |

The β-triketones obtained from selected Myrtaceous volatile oils were shown to have significant insecticidal and/or acaricidal activity.

Example 2

Insecticidal Activity

Initial insecticidal screening against two important arthropod species, two-spotted mite (*Tetranychus urticae*) and diamond back moth (*Plutella xylostella*) lavae highlighted three oils on the basis of efficacy, oil yield, oil profile and ease of recollection (Table 2). Where feasible, the $LD_{50}$ and $LD_{95}$ values were determined.

TABLE 2

Percentage Mortality of Three Efficacious Oils

| Species | Two Spotted Mite % Mortality (0.5%/1.0%) | Diamond Back Moth % Mortality (0.5%/1.0%) |
|---|---|---|
| Backhousia angustifolia | 98/98 | 100/100 |
| Backhousia angustifolia | 100/100 | 100/100 |
| Eucalyptus cloeziana | 100/100 | 70/100 |

Insecticidal tests using the oil from fresh plant recollections and steam distillations varied occasionally and, in this regard, it is believed that improving storage conditions including temperature, light and exposure to air and inclusion of a dessicant can enhance the stability of the active fraction of such oils.

E. cloeziana oil continued to show high potency against both insect tests. This oil exhibited an $LD_{95}$ between 0.04-0.20% (depending on formulation and treatment) against two-spotted mite. An $LD_{95}$ of 0.10% was observed against $1^{st}$ instar lavae of diamond back moth and this rose to 0.78% when tested against $3^{rd}$ instar lavae. In additional preliminary investigations with greenhouse thrips (Heliothrips haemorrhoidalis), a 0.1% concentration of E. cloeziana oil induced 100% mortality.

Additional work was carried out on the E. cloeziana oil to explore the contribution the various components make to the overall efficacy of this oil. Fractions 1, 3, 4, and 5 outlined in Example 3 were screened against two-spotted mite. Fractions 1 and 5 showed no significant insecticidal effect. Fractions 3 and 4, comprising 98% and 99% tasmanone were active and showed little difference to the activity of the whole oil.

This suggests that not only is tasmanone the principle component in the oil, but it is also the principle bioactive constituent. It is also reasonable to assume that as the activity of E. cloeziana oil has been demonstrated against a number of different arthropod species, namely a mite (T. urticae), a caterpillar (P. xylostella) and a thrips (H. haemorrhoidalis), its insecticidal activity is broad in nature.

Example 3

Chemistry

Chemical analysis (GC-MS) of the steam-distilled oils from the collected plants in this work are summarised in Table 3.

TABLE 3

β-Triketone Profiles of Selected Oils

| Plant Source | Principle Component* (%) |
|---|---|
| Backhousia angustifolia -I | Dehydroangustione 85% |
| Backhousia angustifolia -II | Dehydroangustinone (80%) |
| Backhousia angustifolia -III | Angustinone (65%) |
| Backhousia angustifolia -IV | Angustinone (28%) |
| Eucalyptus cloeziana | Tasmanone (84-96%) |
| Melaleuca cajuputi subsp platyphylla | Platyphyllol (64-71%) |

*As determined by gas chromatography

The most promising oils were derived from B. angustifolia, M. cajuputi subsp platyphylla and E. cloeziana and these were then subjected to additional chemical fractionation. The lower insecticidal activity observed in the recollected B. angustifolia (IV) was in part attributed to the lower levels of β-triketone. The level of β-triketone was elevated by the removal of the more volatile monoterpenes using vacuum distillation.

Figure 2:
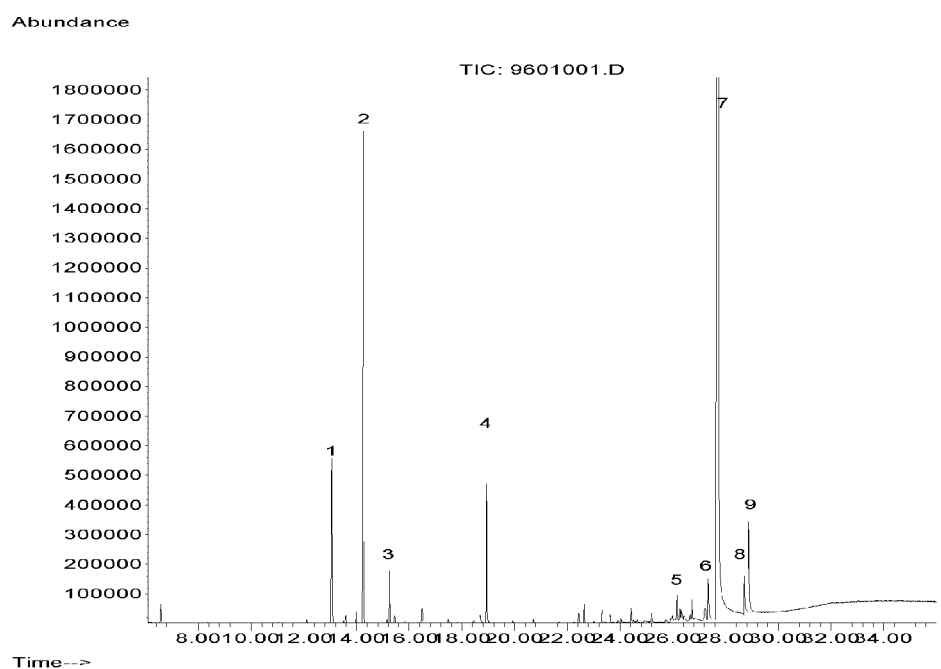
FIG. 2 is a representation of a GC-MS trace of *E. cloeziana* oil.

One of the most efficacious oils was from E. cloeziana, a tasmanone (84-96%) rich oil with additional terpenes and β-triketones (FIG. 2, Table 4), which displayed consistent activity at every stage of processing and formulation. This oil was, therefore, fractionated using column chromatography on silica gel with a hexane-diethyl ether gradient and a final methanol elution. The profiles of the fractions are summarised in Table 5.

TABLE 4

Chemical Profile of E. cloeziana Oil

| Peak No | Compound | Composition (%) |
|---|---|---|
| 1 | a-pinene | 0.5-1.9 |
| 2 | B-pinene | 1.5-5.7 |
| 3 | Limonene | 0.1-0.6 |
| 4 | a-terpineol | 0.7-2.0 |
| 5 | Globulol | 0.01-0.5 |
| 6 | Agglomerone | 0.01-0.6 |
| 7 | Tasmanone | 84-96 |
| 8 | Lateriticone | 0.2-0.7 |
| 9 | Isolateriticone | 0.3-1.2 |

TABLE 5

Fractions Cut From E. cloeziana Oil

| Fraction No | Solvent System | Composition | Amount |
|---|---|---|---|
| F1 | Hexane | Hydrocarbons | 73 mg |
| F2 | Hex:Et2O (9:1) | 80% Tasmanone | 4 mg |
| F3 | Hex:Et2O (1:1) | 98% Tasmanone | 3.66 g |
| F4 | Hex:Et2O (9:1) | +99% Tasmanone | 694 mg |
| F5 | MeOH | Terpene alcohols | 64 mg |

Figure 3:
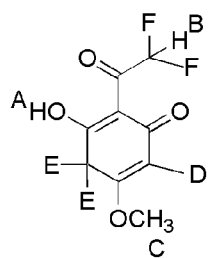
FIG. 3 is a tabular and graphical representation showing $^1$H NMR data recorded on a fraction (F4) obtained from silica gel chromatography of *E. cloeziana* oil and the structure of the major and minor isomers of the compound deduced from these data.
Figure 3:
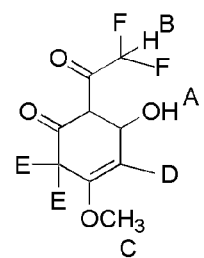
Figure 4:
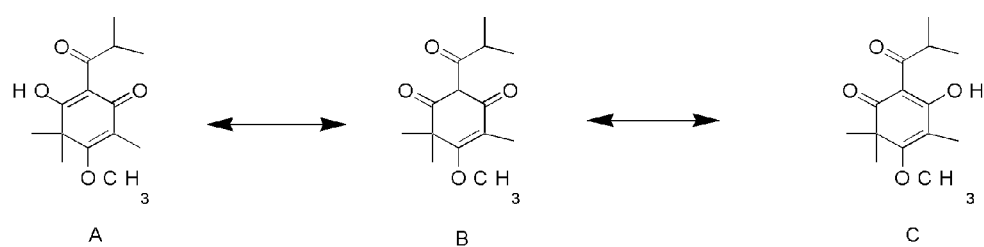
FIG. 4 is a diagrammatic representation showing various tautomeric forms of an isolated β-triketone compound in solution (CDCl$_3$).

$^1$H NMR data (FIG. 3) were recorded on F4 and confirmed the structure of tasmanone. Moreover the compound exists in solution (CDCl$_3$) in tautomeric forms (FIG. 4) in the ratio 2:0:1 (A:B:C).

Another efficacious oils was from M. cajuputi subsp platyphylla, a platyphyllol (64-71%) rich oil (Table 6), which also displayed consistent activity at every stage of processing and formulation.

TABLE 6

Typical Chemical Profile of M. cajuputi subsp platyphylla Oil

| Peak No | Compound | Composition (%) |
|---|---|---|
| 1 | a-pinene | Tr-0.8 |
| 2 | 1,8-cineole | Tr-0.7 |
| 3 | B-caryophyllene | 0.6-3.2 |
| 4 | Humulene | 0.6-1.3 |
| 5 | Spathulenol | 4.0-9.0 |
| 6 | Caryophyllene oxide | Tr-3.6 |
| 6 | Platyphyllol | 64-71 |
| 7 | MW 234 - unknown | 4.3 |

* As determined by gas chromatography

Example 4

Phytotoxicity

Initial investigations using leaves and leaf discs of several plant species including French bean (Phaseolus vulgaris) lemon (Citrus limon) Orange (Citrus sinensis) and Cabbage (Brassica oleracea) indicated that phytotoxicity did not occur for most oils below 0.5%. More detailed investigations using soft intact leaves of young greenhouse-grown French bean subsequently showed *E. cloeziana* oil applied as a spray caused some phytotoxicity at concentrations of 0.5% and above.

Example 5

Toxicity of *E. cloeziana* Oil

Bacterial Reverse Mutation Assay

This study investigated the potential of *E. cloeziana* oil to induce reverse mutations at the histidine locus in the genome of one strain of *Salmonella typhimurium* TA100 in the presence and absence of a metabolic activation system (mammalian microsomal enzymes, S9 mix). The test sample was dissolved in dimethyl sulfoxide (DMSO). In this assay, an *E. cloeziana* oil test sample did not induce an appropriate-fold increase (a 2-fold increase for TA100) in the mean revertants per plate in the tester strain TA100 over the mean revertants per plate of the appropriate vehicle control. Accordingly, the test sample was considered to be non-mutagenic under the conditions of the assay.

Acute Oral

Sighting

The acute oral toxicity of *E. cloeziana* oil was investigated in ten (10) Sprague Dawley Specific Pathogen Free female rats (groups of 2) at doses of 500, 250, 125 and 50 mg/kg. The experimental procedure was based on OECD guidelines for the testing of chemicals, No. 420.

Clinical signs of toxicity occurred between one (1) and twenty-four (24) hours after dosing. Both animals in the 500 mg/kg group exhibited subdued behaviour, partial eye closure, slow breathing, reduced motor activity, ataxia followed by death within 24 hours. The animals in the 250 mg/kg group exhibited subdued behaviour, partial eye closure, slow breathing, social isolation, and reduced motor activity, and had returned to normal by 24 hours after dosing. The animals in the 125 mg/kg group exhibited subdued behaviour, partial eye closure, slow breathing, piloerection and reduced motor activity, and had returned to normal by 24 hours after dosing. The animals in the 50 mg/kg group did not show any signs of toxicity during the seven day experimental period.

There were no other clinical abnormalities in any animal throughout the seven (7) day observation period. The stomach of one animal in the 250 mg/kg group (5F) had a single ulcer. There were no other gross abnormalities in the major organs of any animal at autopsy.

Based on the results obtained from this study 50, 100 and 200 mg/kg can be selected for a main study as the maximum non-toxic dose, intermediate dose and high dose, respectively.

Full Study

The acute oral toxicity of *E. cloeziana* oil was investigated in thirty (30) Sprague Dawley Specific Pathogen Fee rats (15 males and 15 females) at doses of 50, 100 and 200 mg/kg. These doses were chosen following a dose range finding in the above study. The experimental procedure was based on OECD guidelines for the testing of chemicals, No. 420.

The acute NOAEL of *E. cloeziana* oil was determined to be 50 mg/kg, and the MTD was 200 mg/kg under the conditions of this study.

Acute Dermal

The acute dermal toxicity of *E. cloeziana* oil was investigated in ten (10) Sprague Dawley Specific Pathogen Free rats (5 males and 5 females) at a dose of 2000 mg/kg. A preliminary study (SIGHTING) indicated no signs of toxicity at this dose. The experimental procedure was based on OECD guidelines for the testing of chemicals, No. 420.

No clinical abnormalities, skin irritations or body weight losses were observed in any animal throughout the fourteen (14) day observation period. No deaths occurred. No abnormalities were seen in the major organs at necropsy. The rat acute dermal LD50 of *E. cloeziana* oil was determined to be greater than 2000 mg/kg under the conditions of this study.

Skin Irritancy/Corrosion

The potential of a test sample of *E. cloeziana* oil to provoke skin irritation/corrosion reactions was investigated using a primary dermal irritation/corrosion test in three (3) New Zealand White albino rabbits (OECD Guidelines for the Testing of Chemicals, No. 404). The results obtained from this study indicated that *E. cloeziana* oil is a non-irritant according to the National Occupational Health and Safety Commission (NOHSC) "Approved Criteria for Classifying Hazardous Substances [NOHSC:1008 (1999)]".

Example 6

Isolation and Purification of β-Triketones from Australian Myrtaceae Species

Plant collections were commissioned at the Mt. Annan Botanic Garden, Sydney, Australia, and the Darwin Botanic Garden, Northern Territory, Australia to provide potential sources of a range of β-triketone isolation. The plants investigated for β-triketone exploration are listed in Table 6.

TABLE 6

Plants Sourced for β-Triketone Exploration

| # | Source Plant | Plant Location | Accession # | β-triketone anticipated |
|---|---|---|---|---|
| 1 | *Leptospermum morrisonii* | Mt. Annan, NSW | 873247 | grandiflorone |
| 2 | *Eucalyptus bensonii* | Mt. Annan, NSW | 881045 | agglomerone |
| 3 | *Eucalyptus megacornuta* | Mt. Annan, NSW | 831078 | jensenone $^+$ |
| 4 | *Eucalyptus pilularis* | Mt. Annan, NSW | 873166 | torquatone |
| 5 | *Eucalyptus cornuta* | Mt. Annan, NSW | 852618 | jensenone $^+$ |
| 6 | *Eucalyptus baxteri* | Mt. Annan, NSW | 860999 | agglomerone/tasmanone |
| 7 | *Eucalyptus macrorhyncha* | Mt. Annan, NSW | 860896 | conglomerone |
| 8 | *Eucalyptus cloeziana* | Lappa, QLD | PF 2513 | tasmanone |
| 9 | *Melaleuca cajuputi* ssp *platyphyla* | Bensbach, WP, PNG | KW16-19 | platyphyllol |
| 10 | *Eucalyptus jensenii* | NT Botanic Gardens, Darwin, NT | RK114-LUS | jensenone |

TABLE 6-continued

Plants Sourced for β-Triketone Exploration

| # | Source Plant | Plant Location | Accession # | β-triketone anticipated |
|---|---|---|---|---|
| 11 | Backhousia angustifolia | Wilgavale, Texas, QLD | PF1712 | dehydroangustione |
| 12 | Backhousia angustifolia | Didcott Creek, QLD | PF 1708 | angustione |
| 13 | Leptospermum scoparium | NA commercial oil sample | NA | flavesone, isoleptospermone, leptospermone |
| 14 | Eucalyptus conjuncta | Mt Annan | 854097 | conglomerone |

+ Oil contains other β-triketone constituents

All plants, apart from 9 and 13, were steam distilled to yield various quantities of essential oil. All oils were analysed by Gas Chromatography Mass Spectrometry (GCMS) to determine the presence and abundance of β-triketones. Based on this information, particular oils were targeted for isolation and purification of β-triketones using wet chemistry and preparative HPLC techniques.

The β-triketones listed in Table 7 were isolated in quantities adequate for insecticidal screening. A minimum of 50 mg of each compound was required. Isoleptospermone and leptospermone were difficult to separate due to their structural similarity as were angustione and dehydroangustione. Consequently, mixtures of these compounds, where one isomer was significantly more abundant, were provided for insecticidal screening as this will still allow for differentiation in observed activity.

TABLE 7

β-Triketones Isolated for Insecticidal Screening

| β-triketones | Plant source | Sample Purity % by GCMS | Amount sent for screening (mg) |
|---|---|---|---|
| grandiflorone | Leptospermum morrisonii | 100.00 | 99.5 |
| jensenone | Eucalyptus jensenii | 100.00 | 67.9 |
| dehydroangustione | Backhousia angustifolia PF1712 | 95.02 | 165.02 |
| angustione | Backhousia angustifolia PF1708 | 66.30 (33.70% dehydroangustione) | 107.1 |
| agglomerone | Eucalyptus bensonii | 99.28 | 109.2 |
| flavesone | Leptospermum scoparium | 99.32 | 101.8 |
| isoleptospermone | Leptospermum scoparium | 33.10 (66.90% leptospermone) | 113.4 |
| leptospermone | Leptospermum scoparium | 95.33 | 77.0 |
| tasmanone | Eucalyptus cloeziana | 99.92 | 110.1 |
| platyphyllol | Melaleuca cajuputi subsp. platyphylla | 99.62 | 255.6 |

The chemical structures and identities of the β-triketones isolated were confirmed by GCMS and Nuclear Magnetic Resonance (NMR) analysis.

Example 7

Efficacy of *E. cloeziana* Oil on Target Organisms

Target Organisms

Two spotted mite (TSM) *Tetranychus urticae* Koch [Acarina: Tetranychidae] were collected from a mass culture maintained at the University of Western Sydney's Hawkesbury Campus in Richmond, NSW, Australia. They were reared on potted French beans (*Phaseolus vulgaris* L [Fabales: Fabaceae] in a glasshouse maintained at 25±5° C., 65±5% RH and 14 h D:L photoperiod. Only young females were selected for bioassay.

Adult parthenogenetic female greenhouse *thrips* (GHT), *Heliothrips haemorrhoidalis* Bouché (Thysanoptera: Thripidae) of similar age were obtained from a colony reared on orange fruits and maintained in an insectary at UWS Hawkesbury under conditions of 25±3° C., 65% RH and 16 h D:L photoperiod Young nymphs of *citrus* aphids *Toxoptera citricida* (Kirkaldy) (Hemiptera: Aphididae) were collected from lemon seedlings grown under glasshouse conditions at UWS Hawkesbury.

Workers of the termite *Nasutitermes walkeri* Hill (Isoptera: Termitidae) were collected from a laboratory culture at UWS Richmond which was initiated from soil, termitaria and wood on which termites were feeding were field collected at Richmond NSW, and maintained in a darkened container under conditions of 25±2° C., 35-68% RH. Termites were fed on wood collected from near the original nest. Moistened soil from the nest together with paper towel were placed on top of the nest and made it possible to maintain this culture for several months in the laboratory at UWS Hawkesbury.

Workers of the whitefooted house ant *Technomyrmex albipes* (F. Smith) (Hymenoptera: Formicidae) were field collected at UWS Hawkesbury by baiting in an empty glass jar containing sugar granules.

Pupae of housefly, *Musca domestica* L (Diptera: Muscidae) and different stages of American Cockroach, *Periplan-*

*eta americana* L (Blattodea: Blattidae) were initially supplied by C.E.R.I.T and maintained in laboratory culture at UWS Hawkesbury.

Tomato russet mites (TRM) *Aculops lycopersici* (Massee) (Acarina: Eriophyidae) were collected from infested tomato plants near Riverstone, NSW.

Mixed sex adults of the mosquito *Culex quinquefaciatus* (Diptera: Culicidae) were supplied by C.E.R.I.T, held at the in the Centre for Horticulture & Plant Science, University of Western Sydney, Richmond NSW and treated one day after arrival.

Workers of the honeybee *Apis mellifera* (Hymenoptera: Apidae) were collected from several field hives maintained at the apiary in the Centre for Horticulture & Plant Sciences, University of Western Sydney, Richmond NSW Adults of ash-white-flies *Aleaurocanthus woglumi* (Homoptera: Aleyrodidae) were field collected from an ornamental pear (*Prunus* sp) in the Centre for Horticulture & Plant Sciences, University of Western Sydney, Richmond NSW.

Drug store beetle *Sitodrepa panicea* (Coleoptera: Anobiidae) were reared on curry powder under laboratory conditions of 25±1° C. and 65±5% RH.

Mixed age groups of snails *Helix apersa* (Mollusca: Gastropoda) were collected from infested plants in the Centre for Horticulture & Plant Science, University of Western Sydney, Richmond NSW.

Bioassays

TSM

From an *E. cloeziana* oil extract (containing 85% tasmanone), 1.1765 g was dissolved in 5 mL ethyl alcohol and distilled water containing 200 ppm Triton X-100™ was added to prepare a 1% stock solution. From this homogenised stock solution, further serial dilutions of 0.0125, 0.025, 0.05, 0.10, and 0.12% were prepared by mixing the required amount of stock solution in distilled water and Triton X-100 solution. Each treatment was conducted on 60-80 TSM, which were evenly distributed on four French bean leaf discs (25 mm diam) contained in 90 mm diam. petri dishes. The leaf discs were placed with their underside uppermost on moist absorbent cotton wool covered with muslin netting. Water was added to the dishes daily to prevent desiccation of the leaf discs. Five mL aliquots (unless otherwise stated) were applied to each petri dish with a Potter precision spray tower as described by Herron et al (1995). The average mass of solution applied to each dish was calculated to be 3.95 mg/cm$^2$. Mortality was recorded 24 h after treatment. Death was recognised by the absence of movement when the test organisms were mechanically stimulated. Data were analysed using SPSS for Windows™ Version 7. Probit analysis was carried out for dose-mortality data and heterogeneity of regressions was determined by the Pearson chi-squared characteristic.

In addition, TSM was treated with *E. cloeziana* oil extract in combination with paraffin oil. In particular, *E. cloeziana* oil extract at levels of 0.1, 0.2, 0.3, 0.4 and 0.5 g were weighed out and each was made up to a weight of 10.0 g with a formulated paraffin oil (BioPest®), which was then sonicated for 10 min. A 1.0% v/v of each blend was prepared by mixing 1.0 mL with distilled water in a 100.0 mL volumetric flask. TSM were transferred to the petri dish following the same standard method. Five-mL aliquots were applied to each petri dish and mortality was recorded 24 h after treatment. All blends of *E. cloeziana* oil extract with paraffin oil produced 100.0% mortality, compared with Biopest® alone which caused only 35.5±6.9 mortality. The lowest concentration of *E. cloeziana* oil extract tested in this combination (i.e. 0.01%) resulted in 100% mortality in TSM, which is significantly lower than that reported earlier in this document to produce 100% mortality with *E. cloeziana* oil extract alone (>0.06%).

Greenhouse *Thrips*

The same experimental procedure used for TSM was repeated for GHT except that lemon leaf discs were used instead of French beans. The required number of adult *thrips* for each treatment was transferred with a fine brush to the underside of a lemon disc of the same diameter (6 cm) as the base of a petri dish. The lemon disc was mounted on agar with its adaxial side uppermost. Immediately after treatment the petri dish was covered with perforated plastic wrap. Mortality was assessed 24 h after treatment.

Tomato Russet Mite

The same experimental procedure for TSM was repeated except that tomato leaf discs were used instead of French bean.

Brown *Citrus* Aphid

Lemon leaf discs 2.5 cm diam. were cut from tender young leaves and mounted on moistened absorbent cotton wool in 90 mm petri dish with their adaxial surface uppermost. Each petri dish contained four leaf discs. Uniform early instar nymphs were then transferred with a fine brush to the leaf discs (each containing 8-10 nymphs). A Potter tower was used to apply 5 mL aliquots to each petri dish. A control (solvent and surfactant only) was also included in the assessment. Mortality was assessed 24 h after treatment.

Termites

Twenty uniform termite workers were transferred to 90 mm petri dishes lined with the same diameter moistened filter paper (Whatman No 2). A preliminary trial was carried out using a Potter tower to apply 5 mL aliquots of each concentration. Using this method, all termite workers died 4 h after treatment in all concentrations, including the lowest concentration of 0.015%. There was no mortality recorded in the blank control treatment, and all workers remained alive and active for >48 h after treatment. Identical results were obtained from these investigations, whether the petri dishes were covered or uncovered after application of the *E. cloeziana* oil extract.

Subsequent investigations further assessed efficacy of *E. cloeziana* oil extract by releasing termite workers on fresh dried residues. This was carried out by uniformly distributing one mL of each concentration over the entire surface area of a 90 mm diam filter paper. When the paper was air dry, 20 termite workers were placed in each petri dish. One hundred percent mortality was recorded in all four replicates even at the lowest concentration applied (0.015% w/v=150 ppm). This suggests that the plant extract is a highly toxic contact poison to termites.

Ants

The same experimental procedure for termites was repeated for ants, with the required number of worker ants for each treatment transferred with a fine brush to the filter paper containing a fresh dried residue of the *E. cloeziana* oil extract. Immediately after release of the ants the petri dish was covered with perforated plastic wrap, which enabled any excess vapours to escape while retaining the ants. Mortality was assessed 4 h after treatment. In all 4 replicates 100% mortality was obtained at concentrations as low as 0.0075% w/v ai when applied at a rate of 1.0 mL to a 90 mm diam. filter paper.

Houseflies

One percent *E. cloeziana* oil extract was prepared using pure acetone as a diluent. From this solution, further serial dilutions were prepared by adding the required amount in acetone. Five mL aliquots of each concentration of *E. cloeziana* oil extract were dispensed into 500 mL kilner jars. The kilner jars were immediately rotated until dryness to coat the inner surface uniformly with the *E. cloeziana* oil residue. After complete dryness, 30-50 pupae were transferred to a series of clean uncovered petri dishes (45 mm diam.), one of which was placed inside each jar. The jar mouth was then covered with nylon netting supported by a rubber band. All adult houseflies started to emerge from pupae after 48 h and most emerged within a 3 h period. Flies were fed 5% sugar solution soaked in absorbent cotton wool. Jars were maintained in an incubator at 29° C.

Mortality was assessed at the end of the third day (i.e., approx. 72 h) after application of the *E. cloeziana* oil residues in the kilner jar and the placement of pupae inside the jars. (This comprised 48 h for pupae to emerge and 24 h exposure to *E. cloeziana* oil residues which were now 48 h old). Flies were observed to die within a few hours after emergence, whereas in the control they remained alive for >48 h after emergence. The total number of adult houseflies that emerged in each kilner jar was counted and their mortality was recorded.

American Cockroaches

Tests were conducted on 10-20 three months old nymphs (mean individual mass 0.2-0.3 g) and replicated three times. One mL of 1.0% *E. cloeziana* oil extract in acetone was uniformly distributed on 90 mm diam. Whatman No 2 filter paper. A control treatment was also carried out using 1 mL acetone only (i.e., minus *E. cloeziana* oil extract). After complete dryness of the filter paper, the required number of cockroaches was transferred inside the kilner jars, and were fed dry dog food. Kilner jar necks were covered with muslin netting supported by rubber bands. Mortality was assessed 24 h after releasing the cockroaches, and death was recognised by the absence of movement when the test animals were mechanically stimulated.

Adult Mosquitoes

A 0.3576 g of 85% ai of *E. cloeziana* oil extract was dissolve in pure acetone as a diluent to give approximately 0.304% concentration stock solution. From this solution, further serial dilutions 0.152, 0.076, 0.0043 and 0.00215 were prepared by adding the required amount in acetone. Aliquots (2.5 mL) of each concentration of *E. cloeziana* oil extract were dispensed into 500 mL kilner jars with total internal surface area as 286.53 $cm^2$. The kilner jars were immediately rotated to coat the inner surface uniformly with the *E. cloeziana* oil extract residue, until dry. Once completely dry, 10-25 mixed sex adult mosquitoes were released into each kilner jar by allowing the mosquitoes to fly from a darkened cage into the naturally lit jars. The jar mouth was subsequently placed on 110 mm diam. filter paper onto which had been placed a yellow sponge soaked in 7.0% sugar solution. Treated jars were kept under laboratory temperature and humidity conditions, (viz. 24±1° C. and 65±5% RH respectively). Mortality was assessed 24 h after releasing the mosquitoes in the jars.

Honey Bees

Ten worker honey bees, anaesthetised with carbon dioxide, were transferred to 90 mm diam. petri dishes lined with moistened filter paper. Five mL aliquots were applied using a Potter Spray Tower while the bees were still anaesthetised. Yellow sponges soaked in 7% sugar solution were then placed inside petri dishes for bee sustenance, and the bees after treatment were placed in these dishes. The lids that were perforated and covered with muslin netting were placed on the dishes, and mortality was assessed 24 hours after treatment.

Ash White Flies

For each treatment, a 2.5 cm diam. leaf disc was mounted on a moistened Whatman #2 filter paper lining the bottom of petri dishes. Adult white flies were anaesthetised using carbon dioxide and 30-50 adults were transferred onto leaf discs. Serial dilutions of 0.00546, 0.0220, 0.0894 & 0.1788% concentration of *E. cloeziana* oil extract were prepared using distilled water containing 200 ppm Triton X100. Three replicates were treated for each concentration. Five-mL aliquots were applied to each petri dish using a Potter Spray Tower. After treatment, petri dishes were left to dry and then covered with muslin netting. Mortality assessment was assessed 24 h after white flies had been transferred to petri dishes.

Drug Store Beetle

One mL of each concentration of *E. cloeziana* oil extract in pure acetone was uniformly dispensed on 90 mm diam. Whatman No 2 filter paper. The latter was left for 1 h to air dry before being used to line the lid of a 90 mm diam. petri dish. Between 10-15 mixed adults were then transferred into the petri dish, which was sealed with Parafilm™. Mortality assessment was carried out 24 h after sealing the petri dish.

Snails

Two methods were used to assess the efficacy of *E. cloeziana* oil extract against snails. In the first method different age groups of adult snails were dipped directly into a solution of 0.5% concentration of *E. cloeziana* oil extract in distilled water containing 200 ppm Triton X10. Snails were dipped for 10 seconds and thereafter immediately filtered in a sieve. The treated snails were divided in three 500 mL kilner jars containing French bean leaves as a food source. The control was carried out using 0% *E. cloeziana* oil extract. Mortality was assessed 24 h after treatment.

Allowing the snails to crawl on a *E. cloeziana* oil extract contaminated surface carried out the second method. Two mL of 0.08% concentration of *E. cloeziana* oil extract in pure acetone were dispensed in 500 mL kilner jars which were rotated to uniformly cover all inner surfaces until dry. Six different age groups of snails were put into each jar along with plant material for food and covered with muslin netting held by a rubber band. Three replicates of each treatment (0.0 & 0.08% concentration) were carried out. Mortality was assessed 24 h after releasing the snails inside the jars.

The above bioassay results are summarised in Table 8.

TABLE 8

Summary of *E. cloeziana* Oil Extract Efficacy Against Various Target Pests

| Target Pest | $LD_{50}$ (95% CL) | $LD_{95}$ (95% CL) | Method of application | Remarks |
|---|---|---|---|---|
| TSM | 0.07 (0.06-0.08) | 0.14 (0.12-0.16) | Potter spray tower; Aliquot applied 2.5 mL | Knockdown effect observed 2 h after treatment |

TABLE 8-continued

Summary of *E. cloeziana* Oil Extract Efficacy Against Various Target Pests

| Target Pest | $LD_{50}$ (95% CL) | $LD_{95}$ (95% CL) | Method of application | Remarks |
|---|---|---|---|---|
| TSM | | <0.01 | *E. cloeziana* oil extract + paraffin oil | 100% mortality at 0.01% |
| TRM | 0.02 | 0.04 | Potter spray tower | |
| GHT | 0.10 | 0.125 | Potter spray tower | |
| Aphid | 0.08 | 0.30 | Potter spray tower | |
| American cockroach nymph | | 157.27 µg/cm² | *E. cloeziana* oil residues on filter paper | |
| Ant | | <0.0075 | *E. cloeziana* oil residues on filter paper | 100% mortality at 0.0075% when 1 mL applied as residue on filter paper |
| Termite | | <0.0075 | *E. cloeziana* oil residues on filter paper | 100% mortality at 0.0075% when 1 mL applied as residue on filter paper |
| DBM 1$^{st}$ instar larva | 0.09 | 0.20 | 5 mL Potter spray tower | |
| Housefly adult | 69.8 µg/cm² | 130.87 µg/cm² | *E. cloeziana* oil residues on kilner jar wall | |
| Adult mosquitoes | 0.00387 (0.00328-0.00451) | 0.00694 (0.00596-0.01051) | Residues on kilner jar wall | Apparently very rapid knock down. |
| Ash white fly | 0.01773 (0.01179-0.03446) | 0.0.03728 (0.02657-0.08337) | Potter spray tower, 2.5 mL aliquot | Assessed 4 h after treatment |
| Drug store beetle | 0.03548 | 0.37275 | Self contaminating by walking on filter paper | Mortality assessed 24 h after releasing adults. |
| Honeybees | 0.12 | 0.40 | Potter spray tower Aliquot applied 5 mL | Knockdown effect observed 2 h after treatment |
| Snails | ~0.084 | | *E. cloeziana* oil residues on kilner jar wall | Three mL acetone solution for each of 3 replicates. Snails crawled on the wall on dried residues. |
| Snails | | 100% mortality | Dipping method in 0.5% | Three replicates |

Potted Plant Investigations

The efficacy of *E. cloeziana* oil extract against TSM was further assessed under greenhouse conditions. French bean plants were grown in 15 cm diam. plastic pots in an insecticide-free glasshouse maintained at 27° C., RH 65% and natural light. Plants were used when they reached the two true-leaf stage (i.e., before trifoliate leaves appeared). One plant was maintained in each pot (i.e., two leaves/pot). Twenty gravid TSM females were then transferred with a fine brush to the upper surface of each leaf. Mites were left to settle for 4 h before treatment, during which time they usually settled on the lower leaf surfaces. *E. cloeziana* oil extract at a concentration of 0.07% as well as a blank control were prepared using the same procedures described above for the laboratory bioassays. A 400 mL hand sprayer was used to apply the pesticide evenly to all aerial surfaces of the plants, to run-off. Each treatment was replicated four times. The mortality was assessed 24 h after treatment. The results were recorded as mean percent mortality with standard deviation. These results revealed that the mean percent mortality in *E. cloeziana* oil extract treatment and control were 92.19±6.39 and 0.25±0.46, respectively.

In summary, *E. cloeziana* oil extract was efficacious against all pests tested namely TSM, TRM, GHT, aphids, termites, houseflies, American cockroaches, whitefooted ants adult mosquitoes, ash whitefly, drug store beetle and snails. It was also toxic to honey bees.

Example 8

*E. cloeziana* Oil Extract as a Fumigant

An investigation was undertaken to determine the fumigation action of *E. cloeziana* oil extract against arthropods. The test organisms used were termites, *Nasutitermes walkeri*. A Whatman No 2 filter paper (90 mm diam.) was immersed in distilled water five seconds and left to drain excess water before placing it on the bottom of a 90 mm diam. petri dish, to provide moisture for termite workers during the experimental period. A 1.0% *E. cloeziana* oil solution was prepared in pure acetone. One mL was uniformly spread on a second filter paper, which was allowed to air dry on a sheet of aluminium foil. It was then placed under the lid of the petri dishes containing the moist filter paper on their base. Twenty uniform worker termites were transferred to the moist base of each test petri dish, which was subsequently covered with its lid containing the treated filter paper, and the dishes were then sealed with Parafilm™.

A similar series of control treatments was also prepared, using acetone only, for comparison. Five replicates were used in each treatment.

The termites did not move to the dry top surface and remained on the water-moistened filter paper lining the base of the petri dishes throughout the experimental period. Mortality was assessed 5 h after termite release.

The results revealed that *E. cloeziana* oil extract has highly significant fumigant effects on termites. One hundred percent mortality was recorded in all replicates of the *E. cloeziana* oil treatment whereas no mortality occurred in any of the control (acetone only) replicates.

Example 9

Efficacy of Purified β-Triketones Against TSM

The efficacy of purified β-triketones against TSM was investigated using the TSM bioassay described in Example 8. All β-triketones tested demonstrated a high level of activity against TSM (see Table 9).

TABLE 9

Efficacy of β-Triketones Against TSM

| No. | Sample wt (mg) | Chemical Name | $LD_{50}$ and 95% CL | $LD_{95}$ and 95% CL |
|---|---|---|---|---|
| 1 | 109.2 | Agglomerone | 0.15 (0.11-021) | 0.33 (0.22-1.06) |
| 2 | 99.5 | Grandiflorone | 0.04 | 0.13 |
| 3 | 165.0 | Dehydroangustione | 0.36 (0.33-0.41) | 0.69 (0.61-0.81) |
| 4 | 107.1 | Angustione | 0.22 (0.21-0.24) | 0.35 (0.31-0.40) |
| 5 | 67.9 | Jensenone | No direct mortality occurred in any concentration tested (0.05-0.4%) within 24 h. However, all treated TSM were unable to move normally and continued to convulse until they commenced to die 72 h after treatment. There was no recovery. | |
| 6 | 110.1 | Tasmanone | 0.055 | 0.150 |
| 7 | 101.8 | Flavesone | 0.020 (0.006-0.043) | 0.0876 (0.076-0.114) |
| 8 | 77.0 | Leptospermone | 0.037 | 0.169 |
| 9 | 113.4 | Isoleptospermone | 0.043 (0.027-0.057) | 0.071 (0.058-0.109) |
| 10 | 141.1 | Platyphyllol | 0.070 | 0.23 |

Example 10

Efficacy of Purified β-Triketones Against GHT

The efficacy of purified β-triketones against GHT was investigated using the GHT bioassay described in Example 8. All β-triketones tested demonstrated a high level of activity against GHT (see Table 9).

All β-triketones except jensenone caused 100% mortality on GHT at a concentration of 0.3% when 5 mL aliquots were applied with a Potter spray tower. The latter β-triketone did not cause direct mortality within 24 h, but caused behavioural effects at all concentrations tested. Convulsion and lack of movement were consistently observed and 60.0% mortality was recorded 72 h after application in the 0.4% treatment.

Examples 11

| Ready-to-use miticide spray - I | |
|---|---|
| Ingredient | Parts |
| *E. cloeziana* extract | 0.1 |
| Emulsifier: e.g. t-octylphenoxypolyethoxyethanol, polyoxyethylenesorbitan, organosilicate | 1.0 |

-continued

| Ready-to-use miticide spray - I | |
|---|---|
| Ingredient | Parts |
| Solvent: e.g. ethyl alcohol, isopropyl alcohol etc | 5 |
| Tannic acid | 1.0 |
| Carrier e.g. water | 92.9 |

Examples 12

| Concentrated natural emulsifiable concentrate spray (4.4%) - I | |
|---|---|
| Ingredient | Parts |
| *E. cloeziana* extract | 4.4 |
| Pyrethrins | 7.4 |

-continued

| Concentrated natural emulsifiable concentrate spray (4.4%) - I | |
|---|---|
| Ingredient | Parts |
| Emulsifier: e.g. t-octylphenoxypolyethoxyethanol, polyoxyethylenesorbitan, organosilicate | 14.7 |
| Solvent: e.g. ethyl alcohol, isopropyl alcohol etc | 73.5 |

Example 12

| Concentrated emulsifiable concentrate spray (44%) | |
|---|---|
| Ingredient | Parts |
| *E. cloeziana* extract | 22.0 |
| Platyphyllol (natural or synthetic) | 22.0 |
| Emulsifier: e.g. t-octylphenoxypolyethoxyethanol, polyoxyethylenesorbitan, organosilicate | 34.0 |
| Solvent: e.g. ethyl alcohol, isopropyl alcohol etc | 22 |

Example 13

| Natural ready to use insecticide spray | |
|---|---|
| Ingredient | Parts |
| *E. cloeziana* extract | 0.3 |
| Lavender oil | 1.0 |
| Emulsifier: e.g. t-octylphenoxypolyethoxyethanol, polyoxyethylenesorbitan, organosilicate | 1.0 |
| Solvent e.g. ethyl alcohol, isopropyl alcohol etc | 40 |
| Carrier: Water | 57.7 |

Example 14

| Oil-based natural spray concentrate | |
|---|---|
| Ingredient | Parts |
| *E. cloeziana* extract | 10.0 |
| Petroleum oil | 89.0 |
| Emulsifier: e.g. t-octylphenoxypolyethoxyethanol, polyoxyethylenesorbitan, organosilicate | 1.0 |

Example 15

| Concentrated emulsifiable concentrate spray (10%) | |
|---|---|
| Ingredient | Parts |
| *E. cloeziana* extract | 10.0 |
| Permethrin | 10.0 |
| Piperonyl butoxide | 28.0 |
| Emulsifier: e.g. t-octylphenoxypolyethoxyethanol, polyoxyethylenesorbitan, organosilicate | 31.0 |
| Solvent e.g. ethyl alcohol, isopropyl alcohol etc | 21 |

Example 16

| Molluscidal dust | |
|---|---|
| Ingredient | Parts |
| *E. cloeziana* extract | 2 |
| Anti-caking agent (e.g. silica gel) | 2 |
| Emulsifier: e.g. t-octylphenoxypolyethoxyethanol, polyoxyethylenesorbitan, organosilicate | 3 |
| Inert carrier (talc, kaolin, diatomaceous earth) | 93 |

Example 17

| Aerosol insecticidal and acaricidal spray | |
|---|---|
| Ingredient | Parts |
| *E. cloeziana* extract | 1.0 |
| Piperonyl butoxide | 0.9 |
| Propellent hydrocarbon | 98.1 |

Example 18

| Repellent | |
|---|---|
| Ingredient | Parts |
| *E. cloeziana* extract | 19.5 |
| *Citronella* oil | 29.1 |
| Phthalic acid dibutyl ester | 29.1 |
| N-octyl bicycloheptene dicarboxamide | 22.3 |

Examples 19

| Ready-to-use miticide spray - II | |
|---|---|
| Ingredient | Parts |
| *Melaleuca cajeputi* extract | 0.2 |
| Emulsifier: e.g. t-octylphenoxypolyethoxyethanol, polyoxyethylenesorbitan, organosilicate | 1.0 |
| Solvent: e.g. ethyl alcohol, isopropyl alcohol etc | 5.0 |
| Tannic acid | 1.0 |
| Carrier e.g. water | 92.8 |

Examples 20

| Concentrated natural emulsifiable concentrate spray (4.4%) - II | |
|---|---|
| Ingredient | Parts |
| *Melaleuca cajeputi* extract | 8.8 |
| Pyrethrins | 7.4 |
| Emulsifier: e.g. t-octylphenoxypolyethoxyethanol, polyoxyethylenesorbitan, organosilicate | 14.7 |
| Solvent: e.g. ethyl alcohol, isopropyl alcohol etc | 69.1 |

Examples 21

| Ready-to-use miticide spray - III | |
|---|---|
| Ingredient | Parts |
| 99% Tasmanone | 0.09 |
| Emulsifier: e.g. t-octylphenoxypolyethoxyethanol, polyoxyethylenesorbitan, organosilicate | 1.0 |
| Solvent: e.g. ethyl alcohol, isopropyl alcohol etc | 5 |
| Tannic acid | 1.0 |
| Carrier e.g. water | 92.91 |

Examples 22

| Concentrated natural emulsifiable concentrate spray (4.4%) - III | |
|---|---|
| Ingredient | Parts |
| 99% Tasmanone | 4.0 |
| Pyrethrins | 7.4 |
| Emulsifier: e.g. t-octylphenoxypolyethoxyethanol, polyoxyethylenesorbitan, organosilicate | 14.7 |
| Solvent: e.g. ethyl alcohol, isopropyl alcohol etc | 73.9 |

Examples 23

| Ready-to-use miticide spray - IV | |
|---|---|
| Ingredient | Parts |
| 99% Platyphyllol | 0.09 |
| Emulsifier: e.g. t-octylphenoxypolyethoxyethanol, polyoxyethylenesorbitan, organosilicate | 1.0 |
| Solvent: e.g. ethyl alcohol, isopropyl alcohol etc | 5 |
| Tannic acid | 1.0 |
| Carrier e.g. water | 92.91 |

Examples 24

| Concentrated natural emulsifiable concentrate spray (4.4%) - IV | |
|---|---|
| Ingredient | Parts |
| 99% Platyphyllol | 4.0 |
| Pyrethrins | 7.4 |
| Emulsifier: e.g. t-octylphenoxypolyethoxyethanol, polyoxyethylenesorbitan, organosilicate | 14.7 |
| Solvent: e.g. ethyl alcohol, isopropyl alcohol etc | 73.9 |

Example 25

Intra-Specific Crosses for Imparting Pest Resistance to a Pest Susceptible Plant Controlled and wild pollination within *Eucalyptus* and other important commercial Myrtaceae are thoroughly addressed in the CRC for Sustainable Production Forestry Symposium on Hybrid Breeding and Genetics—Controlled Pollination of Eucalypts on 12 Apr. 2000 and published as the proceedings of that symposium. Genetic Pollution from Farm Forestry (Potts et al., 2001) deals more specifically with intra and inter species crosses occurring within the Myrtaceae.

Using the protocols described in the above publications, an intra-specific *Eucalyptus* cross breeding technique will employ the following protocol. This begins with the selection of supreme individuals as parent stock. Within a selected parent stock having superior pest resistant characteristics (e.g., *E. cloeziana*) male and female trees are identified for cross-pollination experiments. Pollen is harvested from the male trees and either stored or directly transferred to the female trees if flowering is synchronous. Emasculation is undertaken to preclude extraneous pollination occurring and flowers are often bagged as a further precaution. Seed set and subsequent embryo development proceeds over the ensuing 12-24 months and F1 seeds are collected at full maturation.

Seeds are then germinated to produce seedlings that are subjected to detailed analysis to assess the transfer of traits from parent to progeny. If the F1 progeny show a desirable mix of phenotypic traits these progeny can be used to vegetatively propagate the new variety. If the F1 progeny show some improvement in the selected phenotypic traits, but further improvement is required selected F1 progeny can be back-crossed either within the F1 progeny or with one of the parent trees to produce an F2 progeny using the methodology outlined above. This iterative process can be continued ad infinitum until the desired characteristics are achieved.

Example 26

Inter-Specific Crosses for Imparting Pest Resistance to a Pest Susceptible Plant Inter-species hybridisation in the wild, which is a common phenomenon within the subgenera of the Myrtaceae, have been recorded at almost 40% in the Eucalypts, 33% in Angophora 19% in Corymbia and 19% in Symphomyrtus. Hybridisation between the major subgenera may also occur (Potts et al., 2001). For example, *Eucalyptus camaldulensis* displays 14 natural hybrid crosses including *E. camaldulensis*×*E. robusta, E. camaldulensis*×*. alba, E. camaldulensis*×*E. cladocalyx, E. camaldulensis*×*E. bigalaterita, E. camaldulensis*×*E. tereticornis, E. camaldulensis*×*E. blakelyi, E. camaldulensis*×*E. dwyeri, E. camaldulensis*×*E. rudis, E. camaldulensis*×*E. ovata, E. camaldulensis*×*E. bridgesiana, E. camaldulensis*×*E. viminalis, E. camaldulensis*×*E. largiflorens, E. camaldulensis*×*E. melliodora, E. camaldulensis*×*E. leucoxylon;* 15 manipulated hybrids including *E. camaldulensis*×*E. diversicolor, E. camaldulensis*×*E. grandis, E. camaldulensis*×*E. botryoides, E. camaldulensis*×*E. cladocalyx, E. camaldulensis*×*E. tereticornis, E. camaldulensis*×*E. blakelyi, E. camaldulensis*×*E. urophylla, E. camaldulensis*×*E. macarthurii, E. camaldulensis*×*E. exerta, E. camaldulensis*×*E. maidenii, E. camaldulensis*×*E. viminalis, E. camaldulensis*×*E. globulus, E. camaldulensis*×*E. gunnii, E. camaldulensis*×*E. laevopinea, E. camaldulensis*×*E. fastigata.* In another example *Eucalyptus globulus* displays 15 natural hybrids including *E. globulus*×*E. barberi, E. globulus*×*E. brookeriana, E. globulus*×*E. ovata, E. globulus*×*E. kitsoniana, E. globulus*×*E. goniocalyx, E. globulus*×*E. nortonii, E. globulus*×*E. cypellocarpa, E. globulus*×*E. pseudoglobulus, E. globulus*×*E. bicostata, E. globulus*×*E. johnstonii, E. globulus*×*E. viminalis, E. globulus*×*E. cordata, E. globulus*×*E. rubida, E. globulus*×*E. urnigera, E. globulus*×*E. perriniana* and 13 successful manipulated hybrids including *E. globulus*×*E. urophylla, E. globulus*×*E. grandis, E. globulus*×*E. robusta, E. globulus*×*E. pellita, E. globulus*×*E. longifolia, E. globulus*×*E. loxophloeba, E. globulus*×*E. camaldulensis, E. globulus*×*E. dunnii, E. globulus*×*E. nitens, E. globulus*×*E. maidenii, E. globulus*×*E. bicostata, E. globulus*×*E. viminalis, E. globulus*×*E. gunnii.* In another example *Eucalyptus grandis* displays 4 natural hybrids including *E. grandis*×*E. urophylla, E. grandis*×*E. robusta E. grandis*×*E. pellita E. grandis*×*E. terreticornis* and 14 manipulated hybrids including *E. grandis*×*E. urophylla E. grandis*×*E. botryoides E. grandis*×*E. pellita E. grandis*×*E. alba E. grandis*×*E. terreticornis E. grandis*×*E. camaldulensis E. grandis*×*E. dunnii E. nitens*×*E. maidenii E. grandis*×*E. globulus E. grandis*×*E. gunnii E. grandis*×*E. pulverulenta E. grandis*×*E. leucoxylon, E. grandis*×*E. resinifera.* In another example the Corymbia henryi/variegata/maculata/citriodora complex displays 14 natural hybrids including *C. citriodora*×*C. catenaria, C. citriodora*×*C. variegata, C. citriodora*×*C. maculata, C. maculata*×*C. gummifrea, C. maculata*×*C. intermedia, C. maculata*×*C. citriodora, C. maculata*×*C. variegata, C. variegata*×*C. bloxsomeri, C. variegata*×*C. watsoniana, C. variegata*×*C. citriodora, C. variegata*×*C. maculata, C. Henryi*×*C. torelliana, C. henryi*×*C. variegata* and onemanipulated hybrid *C. torelliana*×c. In one further example *Eucalyptus cloeziana* displays only 1 natural hybrid *E. cloeziana*×*E. acmenoides*.

The disclosure of every patent, patent application, and publication cited herein is hereby incorporated herein by reference in its entirety.

The citation of any reference herein should not be construed as an admission that such reference is available as "Prior Art" to the instant application Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims. All figures, tables, and appendices, as well as publications, patents, and patent applications, cited herein are hereby incorporated by reference in their entirety for all purposes.

I. BIBLIOGRAPHY

Bignall, C. M., Dunlop, P. J., Brophy, J. J. and Fookes, C. J. R. (1997). Volatile Leaf Oils of some South-western and Southern Australian Species of the Genus *Eucalyptus* (Series I). Part XIV. Subgenus Monocalyptus. Flay Frag. Journal, 12, 177-183.

Boland, D. and J. Brophy (1993). Essential Oils of the *Eucalyptus* and Related Genera Search for Chemical Trends. *Bioactive Volatile Compounds from Plants*. R. Teranishi, R. G. Buttery and H. Sugisawa. Washington D.C., American Chemical Society. 525: 72-87.

Brophy, J. J. and D. J. Boland (1990). "Leaf Essential Oil of Two Chemotypes of *Eucalyptus cloeziana* F. Muell." *Journal of Essential Oil Research* 2(March/April): 87-90.

Brophy, J. J., R. J. Goldsack, et al. (1995). "Leaf Oils of the Genus *Backhousia* (Myrtaceae)." *Journal of Essential Oil Research* 7(May/June): 237-254.

CRC for Sustainable Production Forestry. Symposium on Hybrid Breeding and Genetics—Controlled Pollination of Eucalypts, Noosa Australia, 12 Apr. 2000

Hellyer, R. (1968). "The Occurrence of β-Triketones in the Steam-Volatile Oils of some Myrtaceous Australian Plants." *Aust. J. Chem.* 21(11): 2825-2828.

Herron G A, Beatie G A C, Parkes R A & Barchia I. 1995. Potter spray tower bioassay of selected *citrus* pests to petroleum spray oil. *Journal of Australian Entomological Society* 34: 225-263.

Potts, B M, Barbour, R C and Hingston, A H, 2001. Genetic Pollution from Farm Forestry. Rural Industries Research and Development Corporation Publication (No 01/114).

Southwell, I. A. and J. J. Brophy (2000). "Essential oil isolates from the Australian Flora. Part 3." *Journal of Essential Oil Research* 12: 267-278.

What is claimed is:

1. A method for controlling insects and arachnids, said method comprising exposing the insects and arachnids to a pest-controlling effective amount of the isolated compound flavesone (1-isobutyroyl-3,3,5,5-tetramethylcyclohexan-2,4,6-trione).

2. The method of claim 1, wherein the compound is used in the form of a pest-controlling composition which comprises from about 0.00005% to about 90% by weight of said compound.

* * * * *